Figure 1:
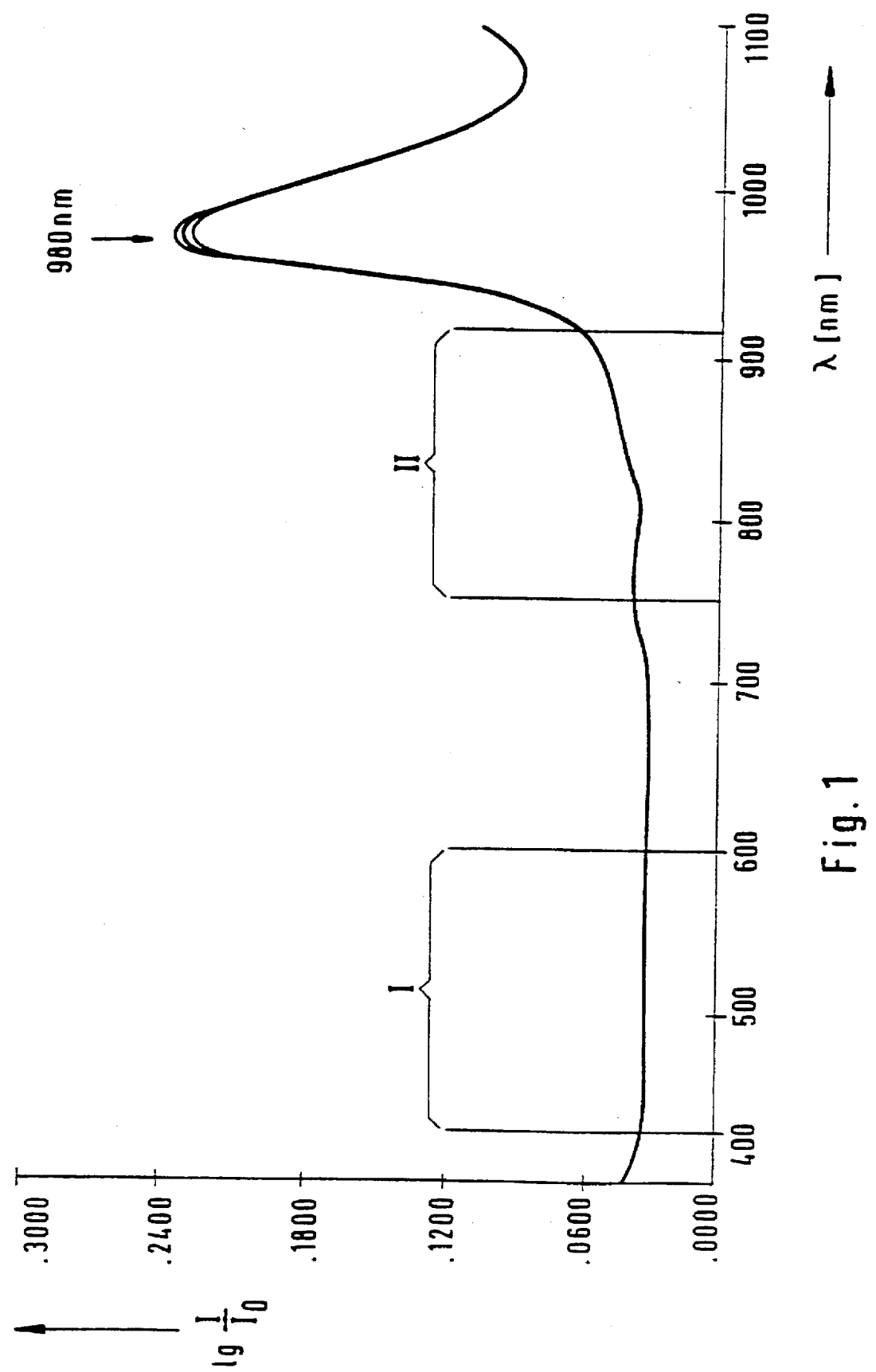

United States Patent [19]
Simonsen et al.

[11] Patent Number: 5,676,143
[45] Date of Patent: Oct. 14, 1997

[54] APPARATUS FOR ANALYTICAL DETERMINATION OF GLUCOSE IN A BIOLOGICAL MATRIX

[75] Inventors: Jan Henning Simonsen, Struer, Denmark; Dirk Boecker, Heidelberg, Germany

[73] Assignee: Boehringer Mannheim GmbH, Mannheim, Germany

[21] Appl. No.: 677,923

[22] Filed: Jul. 10, 1996

Related U.S. Application Data

[62] Division of Ser. No. 271,072, filed as PCT/DE93/01058 Nov. 4, 1993, Pat. No. 5,551,422.

[30] Foreign Application Priority Data

| Nov. 9, 1992 | [DK] | Denmark | 1363/92 |
| Apr. 20, 1993 | [DK] | Denmark | 0446/93 |
| Apr. 21, 1993 | [DK] | Denmark | 0457/93 |
| May 5, 1993 | [DE] | Germany | 43 14 835.2 |

[51] Int. Cl.$^6$ .................................................. A61B 5/00
[52] U.S. Cl. ...................... 128/633; 356/39; 128/664; 128/665
[58] Field of Search .................... 128/633, 664, 128/665; 356/39, 40, 41

[56] References Cited

U.S. PATENT DOCUMENTS

| 3,873,204 | 3/1975 | Friedman et al. | 356/39 |
| 4,014,321 | 3/1977 | March . | |
| 4,223,680 | 9/1980 | Jöbis | 128/633 |

(List continued on next page.)

FOREIGN PATENT DOCUMENTS

| 0 074 428 A1 | 3/1983 | European Pat. Off. . |
| 0 104 772 | 4/1984 | European Pat. Off. . |
| 0 160 768 A1 | 11/1985 | European Pat. Off. . |
| 0 193 868 | 9/1986 | European Pat. Off. . |

(List continued on next page.)

OTHER PUBLICATIONS

Chira et al., *Biomedizinische Technik*, "Light Scattering by Blood Components after Supplying Glucose", vol. 35, Heft May 1990, pp. 102–106.

J. Clin. Chem. Clin. Biochem., vol. 26, No. 4, 1988 Kruse-Jarres: Physiocochemical Determinations of Glucose in vivo. pp. 210–208.

*Primary Examiner*—Jennifer Bahr
*Assistant Examiner*—Eric F. Winakur
*Attorney, Agent, or Firm*—Nikaido, Marmelstein, Murray & Oram LLP

[57] ABSTRACT

An apparatus for determination of a glucose concentration in a biological matrix includes an irradiation device for irradiating light as primary light into a biological matrix, and a detection device for measuring intensity of light emerging as secondary light through the boundary surface of the biological matrix. The detection device detects light from the irradiation device after the light has propagated along a light path in the biological matrix. A data processing device processes measurement signals from the detection device. The irradiation device provides spatially limited illumination of an irradiation site, and the detection device is configured for spatially limited measurements of the secondary light emerging at the detection site. The detection site is located relative to the irradiation site such that the secondary light is multiply scattered at scattering centers in the biological matrix. The irradiation and detection devices are configured to provide at least two different light paths within the biological matrix during detection measurements, and to perform at least two detection measurements wherein the light paths are different. The detection device generates separate measurement signals for each of the at least two detection measurements. The data processing device converts the separate measurement signals into a signal which corresponds to a glucose concentration in the biological matrix.

32 Claims, 11 Drawing Sheets

U.S. PATENT DOCUMENTS

| | | | |
|---|---|---|---|
| 4,295,470 | 10/1981 | Shaw et al. | 128/634 |
| 4,416,285 | 11/1983 | Shaw et al. | 128/634 |
| 4,455,376 | 6/1984 | Maines | 436/63 |
| 4,492,462 | 1/1985 | Pross et al. | 356/39 |
| 4,704,029 | 11/1987 | Van Heuvelen | 128/633 |
| 4,824,242 | 4/1989 | Frick et al. | 356/41 |
| 4,867,557 | 9/1989 | Takatani et al. | 356/41 |
| 4,882,492 | 11/1989 | Schlager | 250/346 |
| 4,883,953 | 11/1989 | Koashi et al. | 250/226 |
| 5,028,787 | 7/1991 | Rosenthal et al. | |
| 5,032,024 | 7/1991 | Cope | 356/41 |
| 5,057,695 | 10/1991 | Hirao et al. | 250/575 |
| 5,086,229 | 2/1992 | Rosenthal et al. | 250/341 |
| 5,127,408 | 7/1992 | Parsons et al. | 128/634 |
| 5,158,082 | 10/1992 | Jones | 128/633 |
| 5,178,142 | 1/1993 | Harjunmaa et al. | 128/633 |
| 5,179,951 | 1/1993 | Knudson | 128/633 |
| 5,204,532 | 4/1993 | Rosenthal | 128/633 |
| 5,277,181 | 1/1994 | Mendelson et al. | 128/633 |
| 5,285,783 | 2/1994 | Secker | 128/633 |
| 5,333,610 | 8/1994 | Hirao | 128/633 |
| 5,337,745 | 8/1994 | Benaion | 128/633 |

FOREIGN PATENT DOCUMENTS

| | | |
|---|---|---|
| 0 160 768 B1 | 5/1989 | European Pat. Off. . |
| 0 353 619 A1 | 2/1990 | European Pat. Off. . |
| 0 426 358 A1 | 5/1991 | European Pat. Off. . |
| 0 527 703 A1 | 2/1993 | European Pat. Off. . |
| 28 51 138 C2 | 11/1977 | Germany . |
| 27 57 196 A1 | 6/1979 | Germany . |
| 28 23 769 | 12/1979 | Germany . |
| 38 28 618 A1 | 8/1987 | Germany . |
| 42 09 886 A1 | 3/1991 | Germany . |
| 40 31 320 A1 | 4/1992 | Germany . |
| WO 89/01758 | 3/1989 | WIPO . |
| WO 90/07905 | 7/1990 | WIPO . |
| WO 91/17697 | 11/1991 | WIPO . |
| WO 92/17765 | 10/1992 | WIPO . |
| WO 93/00856 | 1/1993 | WIPO . |
| WOA 93/11701 | 6/1993 | WIPO . |

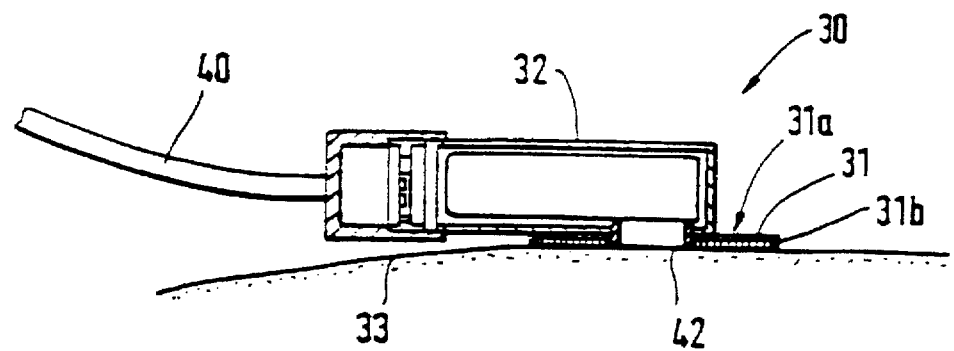
Fig. 13
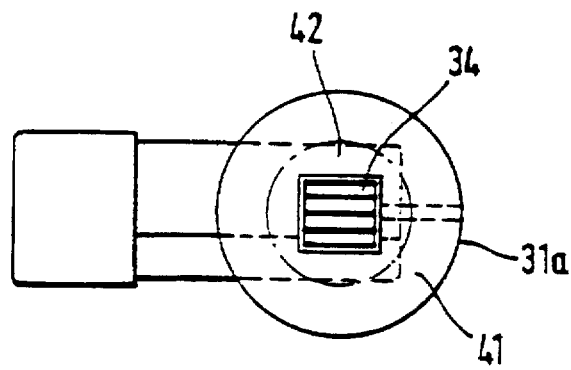
Fig. 14
Fig. 15
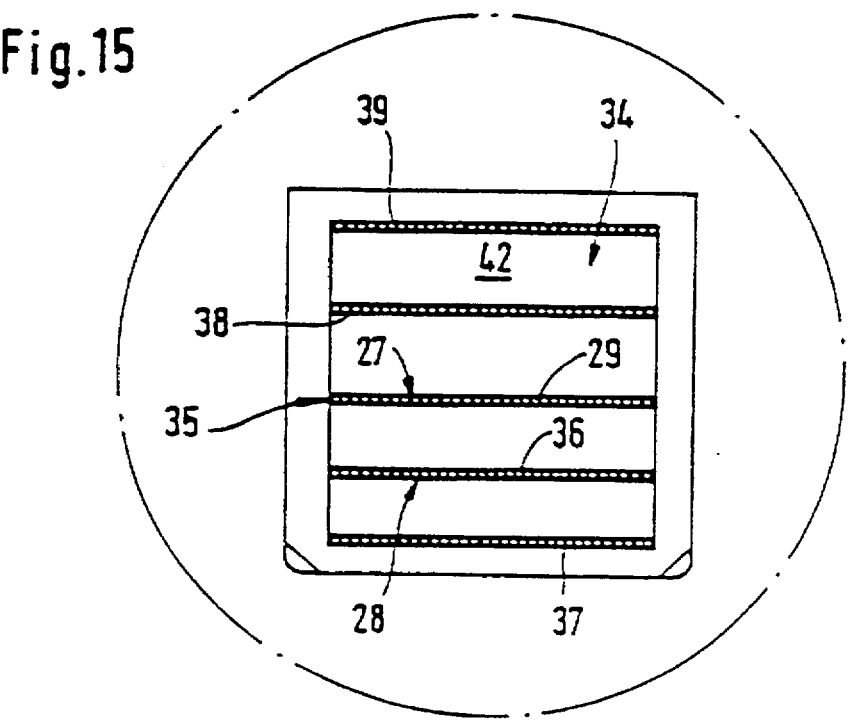

Fig. 21
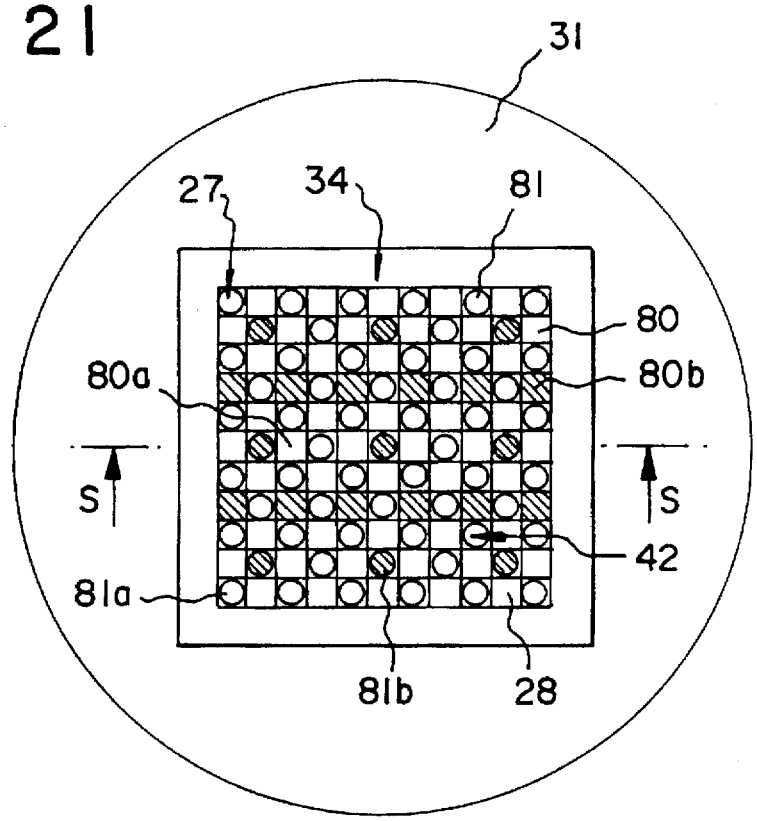
Fig. 22
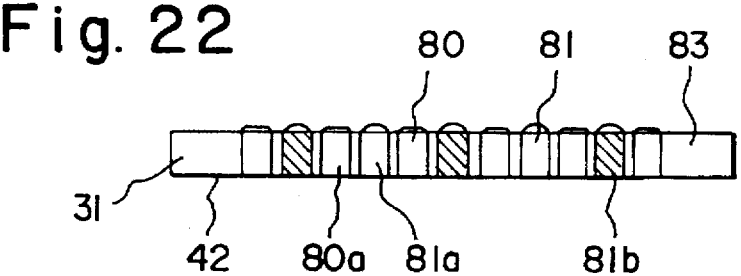
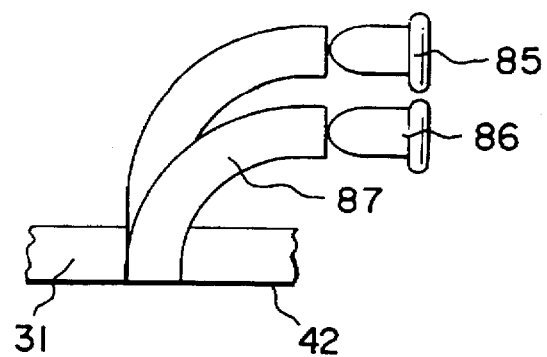
Fig. 23

APPARATUS FOR ANALYTICAL DETERMINATION OF GLUCOSE IN A BIOLOGICAL MATRIX

This is a division of application Ser. No. 08/271,072 filed Jul. 6, 1994, now U.S. Pat. No. 5,551,422, which in turn is a continuation-in-part of International Application PCT/DE93/01058, filed Nov. 4, 1993, and designating the U.S.

The invention relates to a method and an apparatus for the analytical determination of glucose in a biological matrix.

The term 'biological matrix' denotes a body fluid or a tissue of a living organism. Biological matrices, to which the invention relates, are optically heterogeneous, that is, they contain a large number of scattering centres on which radiated light is scattered. In the case of biological tissue, particularly cutaneous tissue, the light-scattering centres are formed by the cell walls and other constituents contained in the tissue.

Body fluids, particularly blood, are likewise optically heterogeneous biological matrices, as they contain particles on which light is multiply scattered. Milk and other liquids investigated in foodstuffs chemistry also often contain a high concentration of scattering centres, for example in the form of emulsified fat droplets.

Reagents or reagent systems whose reaction with the particular component results in a physically detectable change, such as a change in the colour of the reaction solution, which can be measured as a measurement quantity, are generally used for the qualitative and quantitative analytical determination of components of such biological matrices. By calibration with standard samples of known concentration a correlation between the quantity measured at various concentrations and the respective concentration is determined.

These methods allow highly accurate and sensitive analyses, but require the extraction of a liquid sample, especially a blood sample, from the body for analysis ('invasive analysis'). This extraction of a sample is unpleasant and painful and causes a certain risk of infection.

This is especially the case when a disease requires very frequent analyses. Certainly the most important example is diabetes mellitus. With this disease it is necessary to determine the glucose content of the blood very frequently or even continuously if serious secondary diseases and critical states of the patient are to be avoided.

Numerous methods and devices have therefore been suggested for the determination of glucose in blood, tissue and other biological matrices in vivo and non-invasively.

A review of physicochemical (reagent-free) determinations of glucose in vivo is given in J. D. Kruse-Jarres 'Physicochemical Determinations of Glucose in vivo', J. Clin. Chem. Clin Biochem. 26 (1988), pp. 201-208. Nuclear magnetic resonance (NMR), electron spin resonance (ESR) and infrared (IR) spectroscopy are named, among others, as non-invasive methods. However, none of these methods has as yet acquired practical significance. Some of them require extremely large and expensive apparatus, totally unsuitable for routine analysis and certainly for home monitoring of the patient.

The invention relates to a subgroup of non-invasive analysis methods, in which light is irradiated into the biological matrix as primary light through a boundary surface forming the boundary of the biological matrix and the intensity of the light is measured which emerges as secondary light from the biological matrix after interaction. For such a measurement, the term 'detection measurement' is used hereafter. In the known methods several detection measurements are made at different wavelengths for the determination of one glucose concentration. A measurement result which (without the use of reagents) is a measure of the concentration of the analyte in the biological matrix is derived from the spectral dependence of the intensity of the secondary light measured in the detection measurements. The wavelengths of the light considered for such methods are generally between about 300 nm and several thousand nm, hence in the spectral range between near UV- and infrared light. The term 'light' must not be interpreted as being restricted to the visible spectral range of light.

Nearly all known methods of this type are based on the principles of spectroscopy. The fundamental principle is the interaction of the irradiated primary light (of a specific wavelength) with vibration and rotation states of the molecules undergoing analytical determination. The basic vibration and rotation states of glucose are found in the IR region at wavelengths of more than 2500 nm. This spectral range cannot be used for the non-invasive analytical determination of glucose because of the strong absorption of the water, which is always present in high concentration in biological matrices. In the near infra-red (NIR) region the absorption of water is smaller (so-called "water-transmission window"). The spectral analysis of glucose in this region is based on the absorption by overtones and combination oscillations of the basic vibration and rotation states of the glucose molecule (see the article by Kruse-Jarres cited above and EP-A-0 426 358).

The practical making of a non-invasive glucose sensor on the basis of these principles meets with enormous difficulties, which result especially from the fact that the effective signal (the change in the absorption spectrum due to a change in the glucose concentration) is very small and this small signal competes with a large background of interfering signals resulting particularly from the spectral absorption of water and of other strongly absorbing components (among others, the red blood pigment haemoglobin). Many different attempts have been made to solve this problem:

Differential measurements are made at various wavelengths, the first wavelength being chosen so that the glucose absorbs as strongly as possible there, whilst a second wavelength is chosen as reference wavelength so that the absorption is as constant as possible at different glucose concentrations (EP-A-0 160 768).

In U.S. Pat. No. 5,028,787 computer investigations are used to select wavelength pairs which are supposed to be particularly suitable for glucose absorption measurements. The wavelength pair 945 nm and 1015 nm is regarded as particularly suitable.

In WO 93/00856 two wavelengths are selected so that the extinction coefficient is as similar as possible. The intensity of two rays with these two wavelengths is adjusted so that the detected signal is identical. Changes in the glucose concentration are detected as changes in the signal showing the difference between the two wavelengths.

Further processes and apparatus for the non-invasive analytical determination of glucose are described in U.S. Pat. Nos. 5,086,229, 5,178,142, 5,179,951, 4,883,953, 4,882,492 and PCT Applications WO 92/17765 and WO 90/07905.

Despite these endeavours no-one has yet succeeded in providing a practical and functional non-invasive glucose sensor. More realistic is the possibility to use an in vivo sensor based on the principles of spectral analysis for the determination of the concentration of substances with an optical absorption which is several orders of magnitude higher than that of glucose. Important examples are the strongly absorbing haemoglobin (Hb) and its oxidised form HbO2. As these parameters provide information on the oxygenation state of the blood, such sensors are also known as oximeters. Many different designs and methods for non-invasive oximeters are known from the literature. WO 89/01758, U.S. Pat. No. 4,867,557 (corresponding to EP-A-0 286 142), EP-A-0 353 619, EP-A-0 104 772, WO 91/17697, WO 93/11701 (published on Jun. 24, 1993) and U.S. Pat. Nos. 5,057,695, 4,223,680, 4,295,470 and 4,824,242 are for example cited here.

A method and a device for the quantitative determination of glucose by laser light scattering are described in European Patent 0 074 428. Here it is assumed that the glucose molecules scatter a ray of light transmitted through the solution and that the glucose concentration can be derived from this. According to this theory, the principle of the measurement is to obtain the information on the glucose concentration from the spatial angular distribution of the transmitted light emerging from a test cuvette or from an investigated part of the body. In particular, the intensity of the transmitted light is measured in an angular region in which the change in relation to the glucose concentration is as large as possible and is then compared with the intensity measured in the central ray passing directly through the sample. For in vivo analytical determination a transmission measurement on ear lobes with laser light is exclusively recommended.

Similar scientific questions are also discussed in the publication of I. S. Chira et al.: "Light Scattering by Blood Components after Supplying Glucose", Biomed. Technik 35 (1990), pp. 102–106. This investigates experimentally the possibility of determining the concentration of glucose in liquids by the scattering of light. The authors conclude that neither static light-scattering experiments nor by photon correlation spectroscopy (PCS) are suitable for this purpose.

The basic object of the invention is to provide a method for the analytical determination of glucose in a biological matrix which .operates with simple apparatus, without reagents and non-invasively and achieves good analytical accuracy, for example for observing the change of the analyte concentration (continuous monitoring) over a sufficient length of time.

This object is achieved by a method for the determination of the concentration of glucose in a biological matrix comprising at least two detection measurements, in which light is irradiated as primary light into the biological matrix through a boundary surface bounding the biological matrix, the light propagates along a light path within the biological matrix and the intensity of the light is measured which emerges as secondary light from the biological matrix through a boundary surface thereof, and an evaluation step, in which the glucose concentration is derived from the measured intensities of the detection measurements by means of an evaluation algorithm and a calibration, in which at least one detection measurement is a spatially resolved measurement of multiply scattered light in which the primary light is irradiated into the biological matrix at a defined irradiation site, the intensity of the secondary light emerging from the biological matrix at a defined detection site is measured and the detection site is located relative to the irradiation site so that light which was multiply scattered on scattering centres in the biological matrix is detected, the intensity of which is characteristic of the glucose concentration.

The invention also provides a device for the determination of the glucose concentration in a biological matrix, particularly for carrying out the method according to the invention, with a light-transmission area provided for application to a boundary surface of the biological matrix, irradiation means for irradiating light into the biological matrix through one of the boundary surfaces, detector means for measuring the intensity of light emerging through a boundary surface from the biological matrix and data processing means for converting the measured intensity into a signal corresponding to the glucose concentration, in which the irradiation means are designed to provide spatially limited irradiation of a defined irradiation site and the detector means are designed for the spatially limited measurement of the secondary light emerging at a defined detection site, where the detection site is located relative to the irradiation site so that light multiply scattered at scattering centres in the biological matrix is detected, which has an intensity characteristic of the glucose concentration.

It is characteristic of the invention that a measured value characteristic of the glucose concentration can be determined without measuring several wavelengths by two detection measurements being made (preferably at the same measurement wavelength but with different light paths), where at least one of the detection measurements is a spatially resolved measurement of multiply scattered light. In contrast to previously known spectroscopic methods (particularly NIR (near-infrared) spectroscopy), the basis of the measurement of the glucose is not the determination of the optical absorption. Rather the wavelength is preferably chosen in a region of the spectrum in which the absorption by glucose is relatively low.

FIG. 1 shows an absorption spectrum of glucose in water. The decadic logarithm of the ratio of measured intensity to irradiated intensity (lg I/I0) in transmission is shown for a cuvette length of 1 cm and four glucose concentrations, namely 0, 1, 5 and 10%. It can be seen that the spectra for these four concentrations differ slightly only in a small wavelength region at about 980 nm. The maximum signal difference between the measured value with pure water and with 10% glucose solution at this wavelength is less than 2%. At other wavelenghts the difference is even considerably smaller. The variation in the glucose concentration in this experiment is very much larger than the actual physiological glucose concentration. For a realistic glucose change within the physiological range of 100 mg/dl the absorption change at 980 nm is equivalent to less than 0.02%. The change dI/dC in the measurement signal I in relation to the glucose concentration C will in the following be called the "relative signal change" and will be expressed quantitatively in % per 100 mg/dl change of the glucose concentration.

Figure 2:
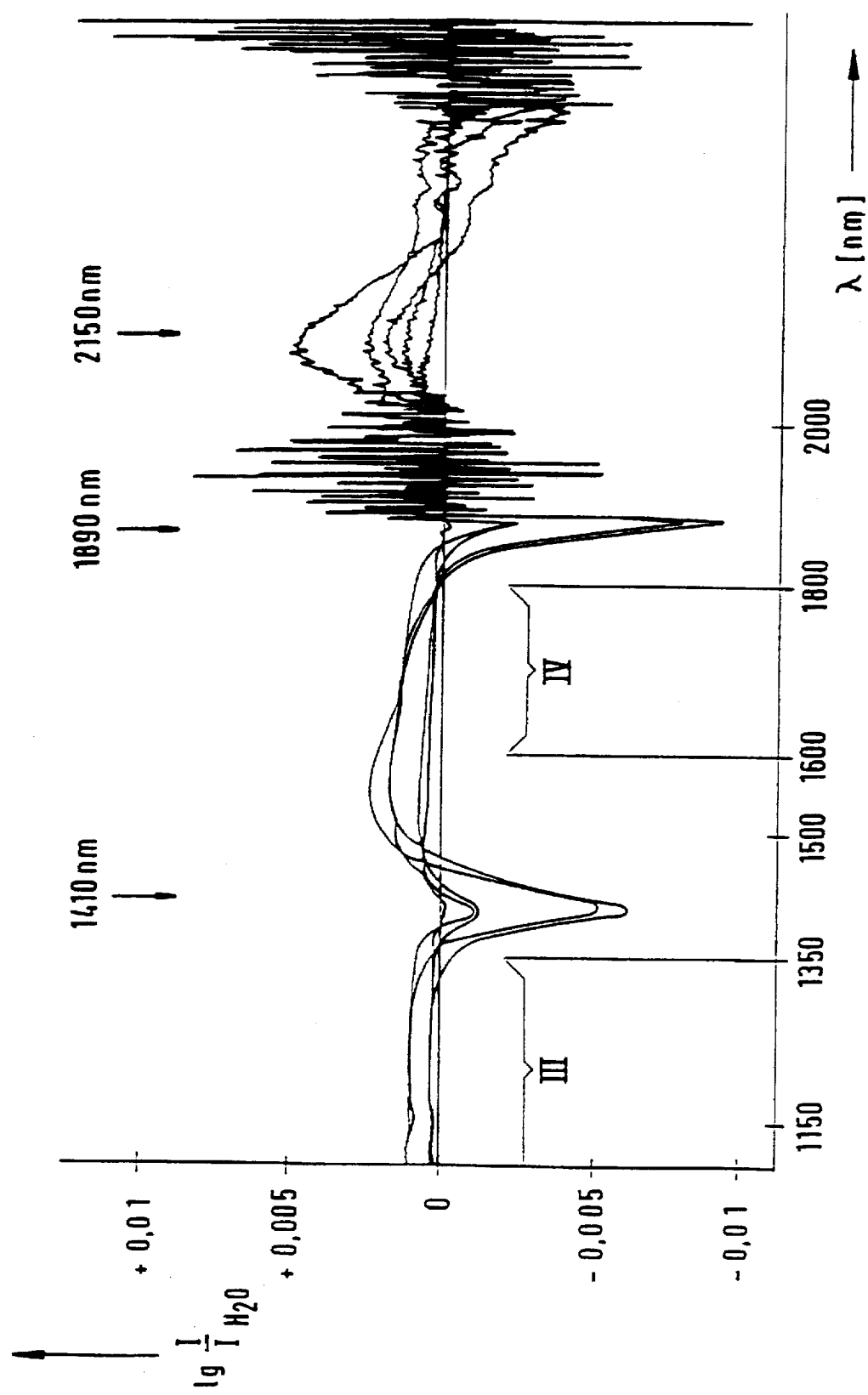

FIG. 2 shows a similar spectrum in the neighbouring wavelength region between about 1100 nm and 2500 nm. This is a differential spectrum for glucose concentrations between 0 and 600 mg/dl compared with pure water. Negative values denote a lower absorption in comparison with pure water. Here the maximum useful change in the signal intensity amounts in total to less than 0.3%, hence on average to less than 0.05% per 100 mg/dl change of the glucose concentration.

FIGS. 1 and 2 together show that the dependence of the absorption on the glucose concentration is so small over wide spectral regions that it is practically useless for measurement in a biological matrix. The wavelength regions in which in a transmission measurement on a clear glucose solution the relative signal change dI/dC is less than 0.01% per 100 mg/dl change of the glucose concentration are referred to as spectral regions with a "small" dependence of the absorption on the glucose concentration.

On the basis of the measurement results shown in FIGS. 1 and 2, the wavelengths at about 980 nm, 1410 nm, 1890 nm and 2150 nm would have to be considered as most suitable wavelengths for spectroscopic analytical determination of glucose.

In the context of the present invention the spectral regions presenting a small dependence of the absorption of an aqueous glucose solution on the glucose concentration can be advantageously used. Specifically, the wavelengths between 400 nm and 940 nm, between 1020 nm and 1390 nm, between 1430 nm and 1880 nm, between 1900 nm and 2050 nm and between 2250 nm and 2500 nm, for example, are suitable. The wavelength regions denoted by Roman numerals in FIGS. 1 and 2 are particularly preferred, namely:

I. 400 to 600 nm.

II. 750 to 850 nm, preferably 780 to 920 nm, particularly preferably 780 to 825 nm or 850 to 900 nm.

III. 1050 to 1350 nm, preferably 1200 to 1300 nm and

IV. 1600 to 1800 nm, preferably 1630 to 1770 nm, particularly preferably 1630 nm to 1670 nm or 1730 nm to 1770 nm.

The measurement should preferably be essentially monochromatic. Here "monochromatic" is to be understood in the practical sense that most of the irradiated and/or emitted intensity is limited to a relatively narrow wavelength region. The half-width (width at half of maximum intensity) should be less than 100 nm and preferably less than 50 nm. In contrast to the spectroscopic methods for non-invasive analytical determination of glucose, relatively broad-banded light sources (with half-widths larger than 20 nm), such as light-emitting diodes or other semi-conductor light sources, can be used without subsequent spectral selection. This considerably reduces the cost of the apparatus. Whenever "the wavelength" of the light source or of the primary light is mentioned here, this expression refers to the wavelength of the maximum intensity.

In contrast to the familiar spectroscopic methods, it is sufficient if the at least two detection measurements are made at only one wavelength. The fact that the measurement signal is substantially independent of the wavelength permits selection of wavelength regions for the measurement in which the smallest possible disturbances caused by strongly absorbing substances occur. In the region around 802 nm the measured intensity is approximately independent of the concentration ratio between Hb and HbO2, as these substances have an isosbestic point there. This is also the case in a broad isosbestic region between 1200 and 1300 nm. Additionally the absorptions of haemoglobin and of water are about the same in this region. This results in a particularly good independence of the measured intensity from the ratio of Hb, HbO2 and H2O.

In the course of the experimental testing of the invention it has been shown that relatively short wavelengths, especially those between 400 and 600 nm, may be particularly advantageous because the depth of penetration of such light in biological tissue is relatively small. The findings of the experiments give reason to believe that this is advantageous particularly because of the more even distribution of the blood in the uppermost dermal layers and possibly also because of better correlation of the glucose concentration with the blood glucose.

Surprisingly on the basis of the present invention a relative signal change dI/dC is found which is much larger than that to be expected on the basis of the absorption even in the narrow wavelength regions, where the absorption of the pure glucose solution is relatively strongly dependent on the glucose concentration. This is true even in wavelength regions where the absorption presents only a small dependence on the glucose concentration. The value of the relative signal change is dependent on the respective measuring apparatus, but in measurements on human skin generally amounts to more than 0.5% per 100 mg/dl and is thus at least ten times greater than the relative signal change that would be expected from the change in the absorption.

According to the inventors' present state of knowledge, this effect may be explained as follows.

The change in the glucose concentration results in a change in the refractive index of the liquid contained in the biological matrix in which the glucose is dissolved. The change in the refractive index results in a change in the light-scattering on the scattering centres contained in the matrix. This change is of course extremely small in each individual scattering process. The change in the refractive index amounts to only about 0.002% per millimole. The inventors have found that this extremely small effect can be put to practical use for the analytical determination of glucose if a large number of scattering processes of many photons that have passed through the biological matrix along a similar light path are detected.

The method of measurement in the invention is therefore designed so that ideally the refractive index-dependent scattering behaviour of the space within the biological matrix surrounding the scattering centres is determined. It has been found that this mechanism of the invention is very sensitive, that is, the change of the measurement signals is relatively large with relatively small changes in the glucose concentration. The increased sensitivity compared with known processes for the in vivo analytical determination of glucose also leads to improved selectivity, since the variation of the multiple scattering used in accordance with the invention depends in the most important biological matrices—blood and dermal tissue—essentially only on the glucose concentration.

This surprising effect may be explained by the multiple scattering which is used in the present invention for the analytical determination of glucose. The method of the instant invention can therefore also be called Multiple Scattering Amplified Glucose Detection (MSAGD).

On the basis of the present invention it is to be assumed that the effect underlying the MSAGD represents a considerable disturbance in spectral analytical determinations of other components of an optically heterogeneous biological matrix. It can therefore also be advantageous to carry out at least one spatially resolved measurement of multiply scattered light in such a spectral-analytical method for correction of changes in the optical path length caused by changes in the glucose concentration. Such a method is likewise a subject of the present invention.

MSAGD differs fundamentally from the methods used hitherto for non-invasive analytical determination in the requirement of multiple scattering. In infrared spectroscopy, which is based on the measurement of the dependence of absorption on wavelength, optical scattering is felt to be disturbing. If at all possible, parts of the body that cause as little scattering of light as possible are therefore selected. It has for example been suggested that NIR spectroscopic determinations should be carried out on the anterior chamber (atrium) of the eye, which contains a relatively clear and therefore non-scattering liquid (U.S. Pat. No. 4,014,321).

Figure 3:
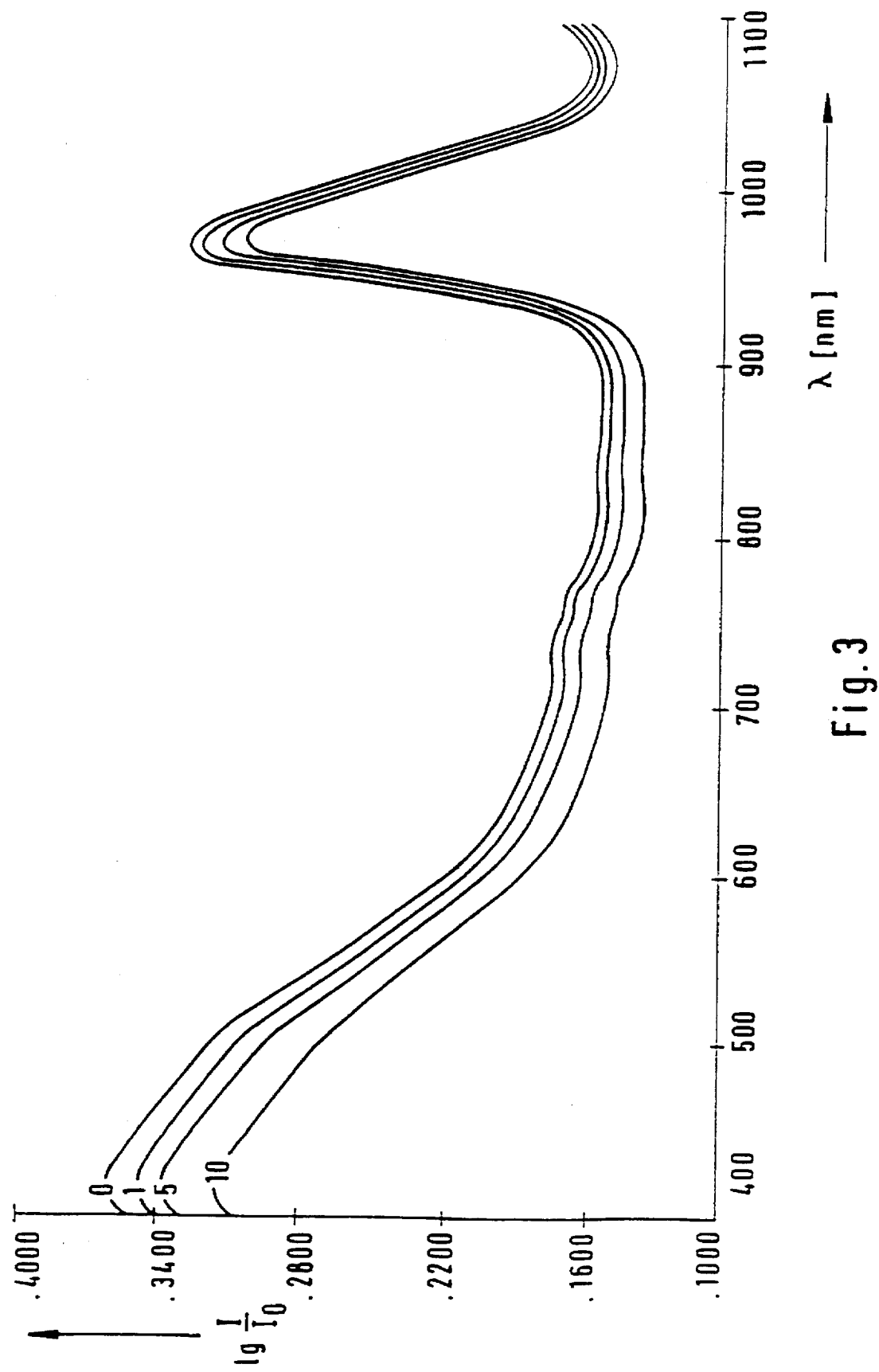

For better understanding, the results of a laboratory experiment are represented in FIG. 3. To the glucose solution, the spectrum of which is shown in FIG. 1, milk with a fat content of 3.5% was added in a concentration of 0.1% by volume under otherwise identical conditions of measurement. A substantial increase in the relative signal change dI/dC, which is particularly large at short wavelengths but in total shows only a slight, continuous dependence on wavelength, is apparent in the entire represented spectral region. The addition of milk converts the clear glucose solution into an optically heterogeneous matrix, in which dispersed milk droplets cause the MSAGD effect.

Comparison of FIGS. 1 and 3 shows that the MSAGD signal also differs from absorption measurements in that the concentration-dependent change in the intensity (dI/dC) is substantially independent of the wavelength. A certain change in the glucose concentration consequently results in a roughly equal change in the intensity of the secondary light, even when the wavelength of the irradiated light differs for example by 100 nm. In contrast to this, the change dI/dC is substantially larger in a more strongly absorbing wavelength region (absorption band) than in a weakly absorbing wavelength region if the detection measurement is based on the absorption of glucose. This is used in spectroscopic measurements by selecting a strongly absorbing wavelength as the measurement wavelength and a weakly absorbing wavelength as the reference wavelength. For this purpose a narrow-band (highly dispersive) measurement (with half-width of less than 10 nm, and often less than 1 nm) in a broad spectral region is necessary.

With the invention no narrow-band measurement is necessary, because of the minimal dependence on the measurement wavelength. Inexpensive semiconductor light emitters (in particular, light-emitting diodes) can therefore be used without the need for additional measures for selecting the wavelength on the primary side or the secondary side. If several light emitters with the same wavelength are to be used, adequate equality in the context of the invention is achieved when commercially obtainable semiconductor light emitters with the same nominal wavelength are used. An apparatus in accordance with the invention can therefore be constructed so as to be particularly small, light and inexpensive. It is consequently especially suitable for the continuous monitoring of a diabetic's glucose concentration.

It is essential for the measurement of the MSAGD effect on actual biological matrices that the conditions of spatially resolved measurement of multiply scattered light (hereinafter abbreviated to "spatially resolved scattered light measurement" (SRSLM)) are met, that is, the "site-dependence condition" and the "multiple scattering condition" must be observed.

The site-dependence condition is to be understood in that the measurement of the secondary light (in contrast to EP-A-0 074 428) is not directed to the light rays scattered or reflected from the matrix in a certain direction or angular region (angle-dependent measurement), but to a defined subregion (area, locality) of a boundary surface of the biological matrix, which is called the detection site. The primary light is also irradiated in a defined subregion of a boundary surface of the biological matrix, which is called the irradiation site. Such a measurement is called a "site-dependent detection measurement".

The terms "irradiation site" and "detection site" are thus to be understood geometrically, namely as the subregion of the boundary surface of a biological matrix at which the light rays decisive for the intensity measured in the respective detection measurement pass through the boundary surface. In the following the term "transition site" will therefore be used as a collective term for the irradiation site and the detection site. Any statements made in the following on distances between transition sites refer respectively to the centres of the irradiation site and of the detection site. The centre in a circular site is formed by the middle point and in a longitudinal site by the midline.

The "multiple scattering condition" is to be understood in that the transition sites (i.e. the irradiation site and the detection site) are arranged in relation to each other so that light which is multiply scattered on scattering centres in the biological matrix the intensity of which is characteristic of the glucose concentration is detected. The following is to be observed in this context.

The mean free path length of photons in the tissue or in the above-mentioned body fluids is dependent on the wavelength and on the respective density and size of the scattering centres. It is typically between about 0.01 mm and 0.1 mm. At least about 10, and preferably at least about 100 scattering processes should take place on the light path in the biological matrix from the irradiation site to the detection site. The light path within the biological matrix is always longer (often even considerably longer) than the direct connection between the irradiation site and the detection site. However, as a practical rule it may be stated that the distance between the irradiation site and the detection site should correspond to at least ten times and preferably to at least twenty times the mean free path length of the photons in the respective biological matrix at the respective wavelength of the primary light.

The maximum distance between the irradiation site and the detection site is likewise dependent on the mean free path length of the photons. Above a limit that is to be determined experimentally in the individual case the intensity of the signal becomes so small that the signal-to-noise ratio is insufficient. The distance between the irradiation site and the detection site should preferably be less than 30 mm and particularly preferably less than 15 mm. Furthermore, careful shielding of the primary light from the detector used to measure the secondary light must be ensured if only light multiply scattered at scattering centres in the biological matrix is to be detected and measured.

The multiple scattering causes the light emerging at the detection site to have a substantially diffuse character, that is, its intensity is substantially independent of the exit angle under which it is detected. If the primary light is coherent and/or polarised, the multiple scattering causes these properties to be substantially lost. It is therefore generally not necessary in the invention (in contrast to EP-A-0 074 428) to use a laser as the primary light source. The degree of polarisation retained in the secondary light may also be used to test whether the "multiple scattering condition" required for the invention is met. The degree of polarisation of the secondary light should for example be less than 10% of that of an irradiated polarised primary light.

The irradiation site and the detection site in SRSLM can have very different dimensions and geometric shapes. The only essential factor is that SRSLM provides information on the intensity of the secondary light in dependence on the relative position of the irradiation site and the detection site (in contrast to a dependence on the angle of detection). A number of such spatially resolved measurements of multiply scattered light in which the respective detection site is at a varying distance from the corresponding irradiation site thus provide information I(r) on the functional dependence of the intensity I on the distance r.

The irradiation site and especially the detection site can generally have relatively large dimensions in SRSLM. However, embodiments in which the transition sites in the direction of the distances connecting the particular irradiation sites and detection sites (the shortest connection) have a relatively small dimension of preferably less than 2 mm and particularly preferably less than 1 mm, are especially preferred.

In spatially resolved measurement of multiply scattered light the detection site is preferably located on the same boundary surface as the irradiation site, i.e. SRSLM is performed 'in reflection'. However, if two boundary surfaces or areas of the biological matrix facing each other are accessible, measurement can also be made 'in transmission', where the irradiation site and the detection site are located on opposite boundary surfaces of the biological matrix. Here, in view of the diffuse nature of the light emerging at the detection site, the terms 'transmission' and 'reflection' are of course not be understood to mean that the secondary light emerges from the matrix in a strongly dominant preferred direction.

The measured intensity values of at least two detection measurements are used in the invention to determine ('derive') the glucose concentration in an evaluation step of the method with the aid of an evaluation algorithm and a calibration. At least a first of these detection measurements must be an SRSLM. In a second detection measurement in principle a different arrangement can be used.

Particular preference is however given to an embodiment in which at least two spatially resolved scattered light measurements are carried out, from the measured intensity values of which the glucose concentration is derived. It has been found that particularly interference-free and thus precise information about glucose concentration can be obtained from the dependence I(D) of the intensity I on the measurement distance D, which can be determined with at least two spatially resolved scattered light measurements. In this procedure the two or more spatially resolved scattered light measurements are carried out at the same wavelength. If more than one light emitter is used, it is sufficient if their wavelengths coincide within the limits of normal series production variations for light-emitting diodes of the same nominal wavelength.

It is of course also possible to carry out a larger number of spatially resolved scattered light measurements and to use them collectively in order to derive the glucose concentration. For at least two of these measurements the light paths should differ substantially from one another. In a spatially resolved scattered light measurement, the term "light path", because of the multiple scattering in the biological matrix, is of course not to be understood in the sense of a geometrically strictly limited fractional volume of the biological matrix (as in the case of a classic transmission spectroscopy of a non-scattering liquid in a cuvette). It nevertheless makes sense to use the term "light path". It may be understood, for example, as the fractional volume of the biological matrix in which a specific percentage (for example, 70%) of the light is transported which, coming from a particular irradiation site, reaches a particular detection site and which is multiply scattered in the matrix.

In practice a different light path is produced in two spatially resolved scattered light measurements by the fact that the measurement distances between the irradiation site and the detection site are sufficiently different. The difference in intensity of the secondary light (relative to an equal area of the detection site and with equal intensity of the irradiated primary light) caused by the different light paths should amount to at least a factor 3, preferably to at least a factor 5 and particularly preferably to at least a factor 10.

The fact that several detection measurements are carried out at the same measurement wavelength but with a different measurement distances between the irradiation site and the detection site constitutes a fundamental difference compared with conventional spectroscopic processes. In spectroscopic methods for obtaining a value of the analyte concentration, detection measurements are carried out at several wavelengths but with a completely identical measurement distance. Any change in the measurement distance would falsify the result of the measurement.

Particularly preferred is an embodiment in which at least two spatially resolved scattered light measurements with an equal measurement distance between the irradiation site and the detection site are made and in which at least either the irradiation sites or the detection sites but preferably both the irradiation sites and the detection sites are different. Advantageously such measurements are made for each of two different measurement distances.

Such an embodiment appears at first sight not to be useful, as two measurements on the same biological matrix with a light path of equal length would produce the same result, that is, no additional information would be acquired by the additional measurement. Expressed in terms of information technology, the additional measurement with the same measurement distance is redundant. However, it was found in the invention that such redundant measurements are advantageous, as they allow the recognition and elimination of potential measurement errors caused by inhomogeneities in the biological matrix (especially in cutaneous tissue).

The at least two detection measurements are preferably made simultaneously or with a sufficiently short interval between them. By sufficiently short we mean here a time interval between the measurements used to derive the glucose concentration in which no change in the biological matrix takes place which would be detrimental to the accuracy of the measurement. This is preferably achieved with an apparatus provided with switchable irradiation means and/or detection means that allow the selection of different pairs of transition sites without moving parts.

Although measurements at one wavelength are sufficient, it can obviously be useful to make measurements at further additional wavelengths, especially to allow better elimination of interfering factors. These interfering factors include, among other things, possible changes in the scattering centres and also the water absorption and the haemoglobin absorption, which in turn depend directly on the blood volume in the investigated biological matrix. Connected with this is the fact that the intensity of the secondary light is influenced by the blood pulse and the body temperature. However, these influences can be controlled. As regards the blood pulse, either the mean can be determined over a sufficient number of pulse periods, or the measurements can be made in synchronism with the pulse. Variation of body temperature can be plotted and used for compensation. Alternatively, the detection area in which the transition sites are located is actively thermostatted. As a relatively high energy consumption is associated with such a temperature regulation, the measurement area in an apparatus for in vivo analytical determination should be carefully thermally insulated.

An evaluation algorithm and a calibration are required in the evaluation step for deriving the glucose concentration from the measured intensities. In this respect the invention does not differ substantially from known analytical determination methods, which likewise—as explained above—require a calibration for assigning the measured quantities (for example, the colour change in colorimetric tests) to the respective concentration.

In the simplest case the algorithm in the present invention comprises a simple predetermined mathematical operation for deriving an intermediate value from the measured intensities I of the detection measurements. The intermediate value can be called the measurement result R. The formation of a simple ratio between the measured intensities of the first and second detection measurements has been found suitable in practice. The measurement result R may then be linked with the glucose concentration C in the familiar manner by calibration with at least two, but preferably with several standard samples of known glucose concentration.

Mathematically more sophisticated methods have recently been increasingly used in analytical technology for improving the correlation between the measured quantities and the respective concentration (and hence the analytical accuracy). These include exponential or logarithmic calculations and iterative methods for optimal description of the relation. Furthermore, it can be advantageous for the improvement of the analytical accuracy to compensate by means of correlation methods influential factors (particularly the temperature at the measurement site and the pulse, for example) that affect the measured intensity as well as the glucose concentration. Multilinear and non-linear mathematical algorithms can be used for the detection and determination of a large number of factors which influence the evaluation of analytical measurements. This is also possible in the present invention and can be advantageous, particularly when a large number of detection measurements are being made with various pairings of transition sites which together form the basis of the analytical determination. In this case the use of learning systems (neuronal networks) can also be advantageous.

Comprehensive additional information about evaluation algorithms suitable for linking the results of detection measurements to the appropriate analyte concentration can be found in the publications mentioned earlier.

The invention is illustrated more fully by the embodiments schematically represented in the following Figures:

FIG. 1 An absorption spectrum of glucose in water in a first wavelength region for various glucose concentrations.

FIG. 2 A differential absorption spectrum of glucose in water against pure water in a second wavelength region for various glucose concentrations.

FIG. 3 A spectrum corresponding to FIG. 1 after addition of milk to the glucose solution.

Figure 4:
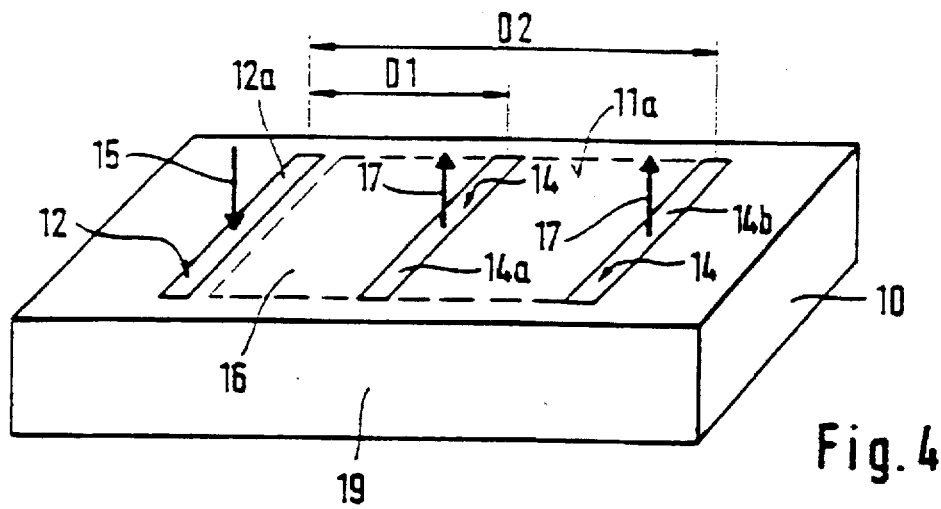

FIG. 4 A perspective representation of the principle of a first embodiment of the invention.

Figure 5:
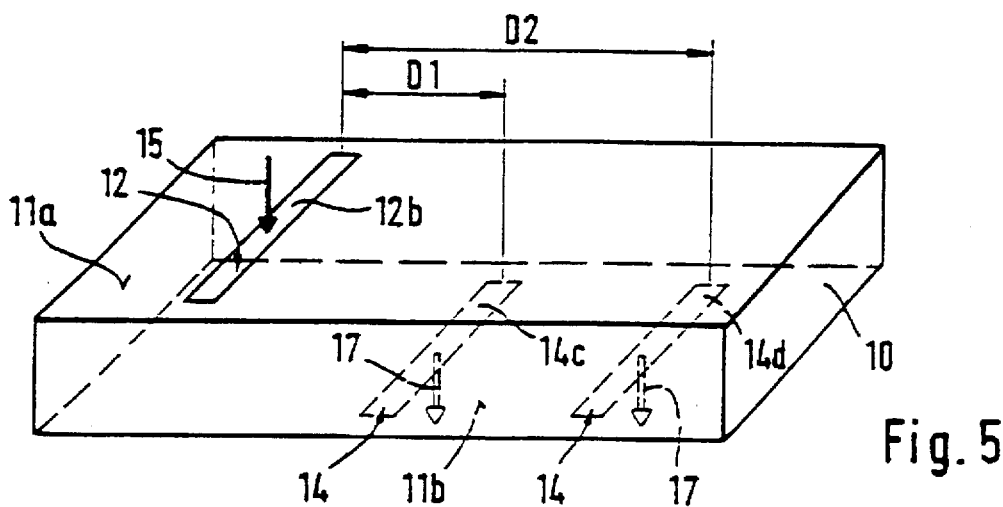

FIG. 5 A perspective representation of the principle of a second embodiment of the invention.

Figure 6:
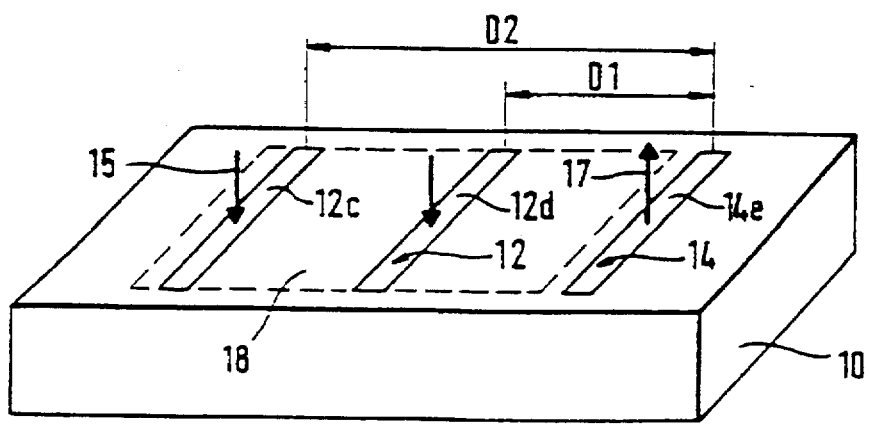

FIG. 6 A perspective representation of the principle of a third embodiment of the invention.

Figure 7:
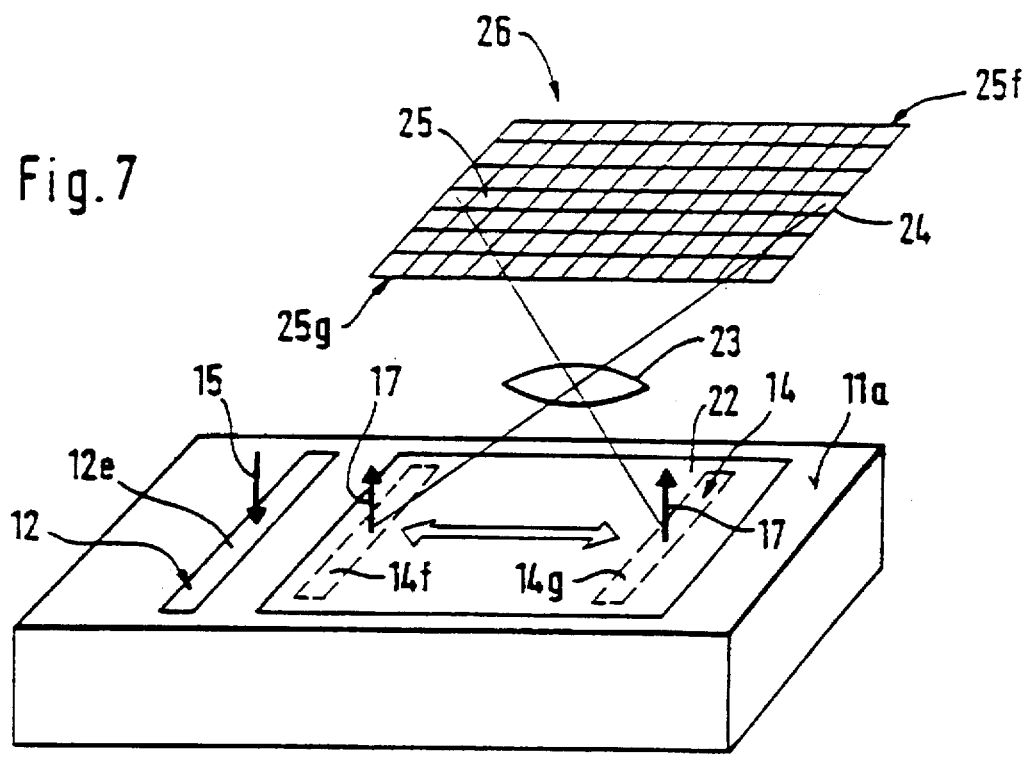

FIG. 7 A perspective representation of the principle of a fourth embodiment of the invention.

Figure 8:
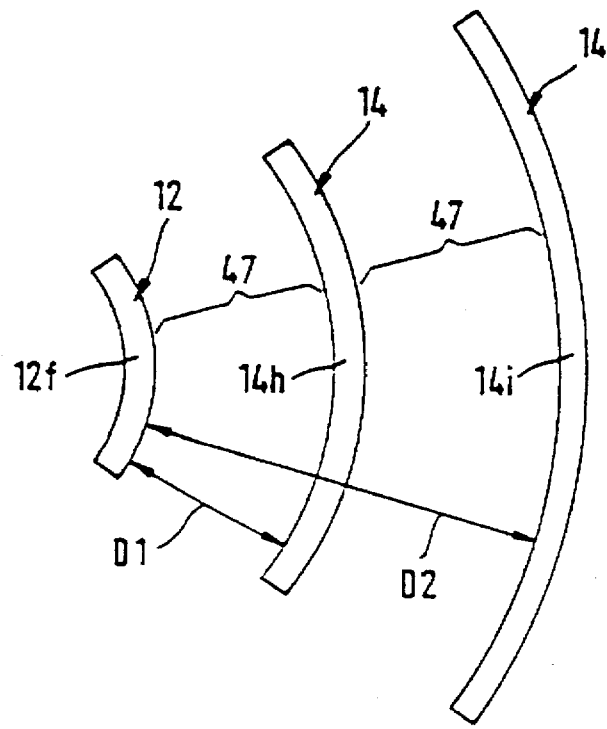

FIG. 8 A representation of the principle of an irradiation field and of a detection field in plan view in a fifth embodiment of the invention.

FIGS. 9 to 12 Representations of the principle of various arrangements of irradiation sites and detection sites on a boundary surface of a biological matrix.

FIG. 13 A sectional representation of a practical embodiment of a suitable measuring head for the invention.

FIG. 14 A view of the measuring head of FIG. 13 from the underside which is contact to the biological matrix.

FIG. 15 An enlarged representation of a section of FIG. 14.

Figure 16:
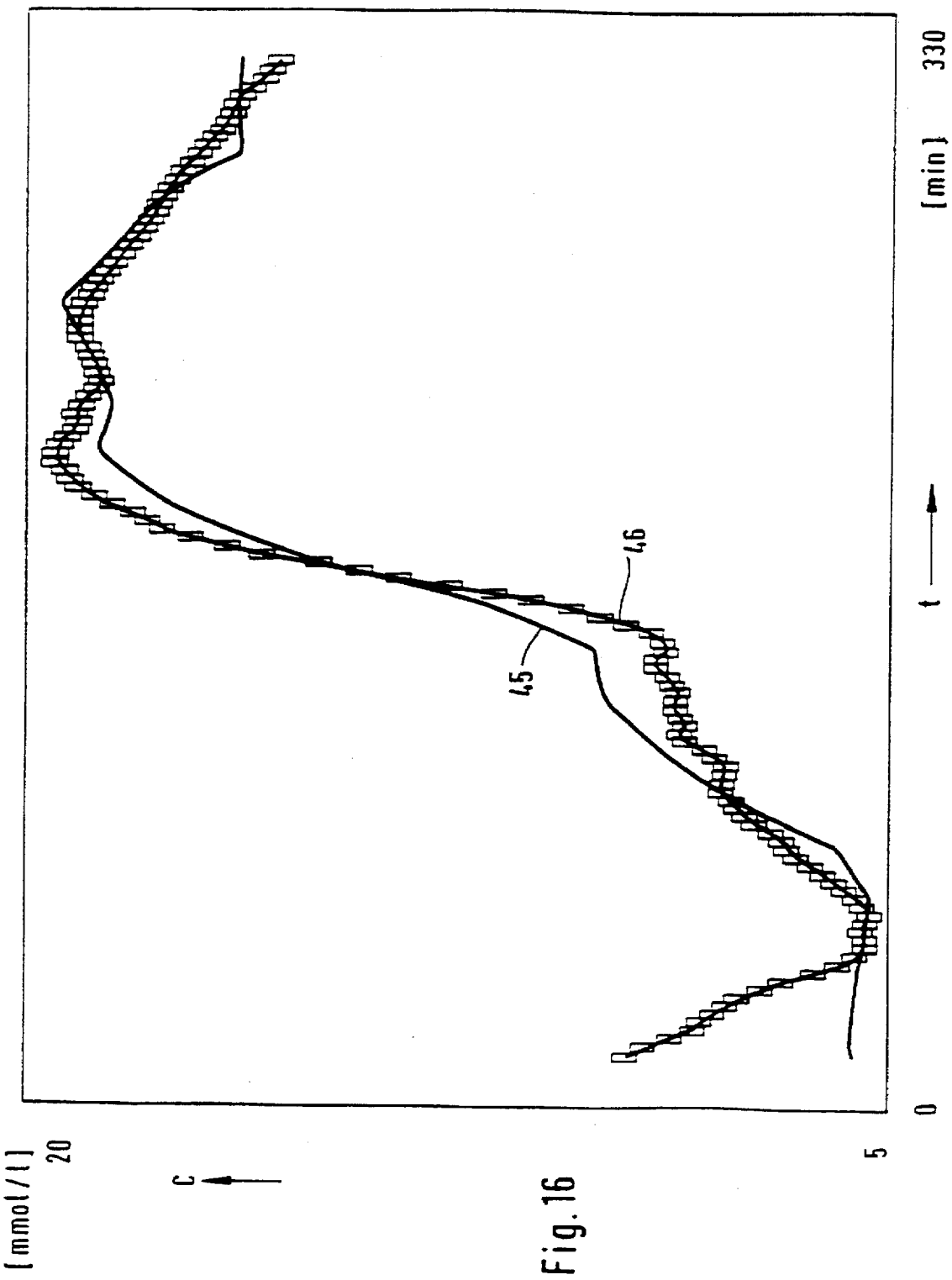

FIG. 16 A graphical comparison of the analysis results obtained with the invention and with a reference method.

Figure 17:
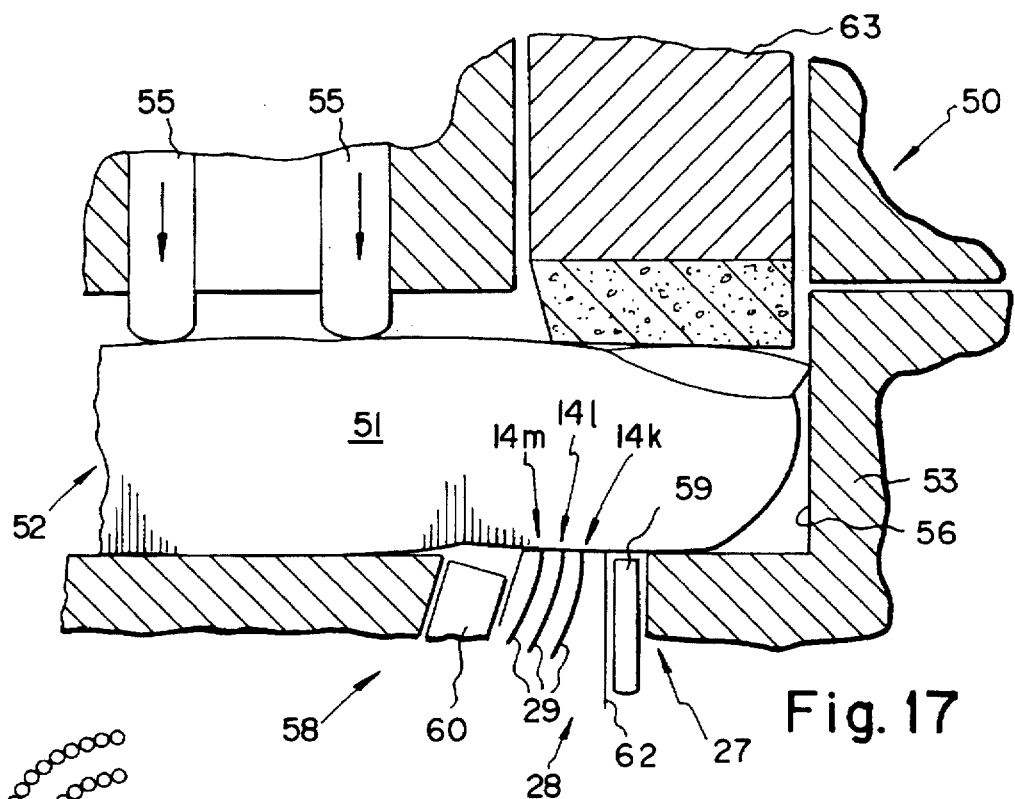

FIG. 17 A lateral cross-sectional representation of a measuring device for analytical determination on the finger.

Figure 18:
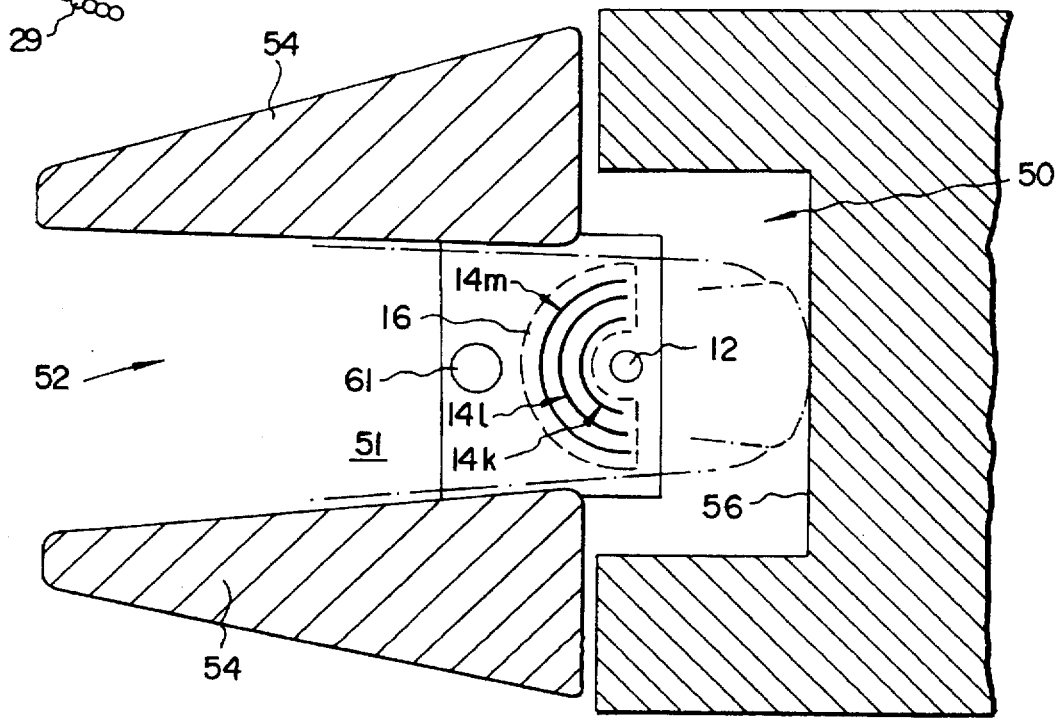

FIG. 18 A plan-view cross-sectional representation of the embodiment of FIG. 17.

Figure 19:
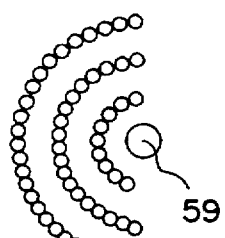

FIG. 19 A plan view of the measuring device in an embodiment according to FIGS. 17 and 18.

Figure 20:
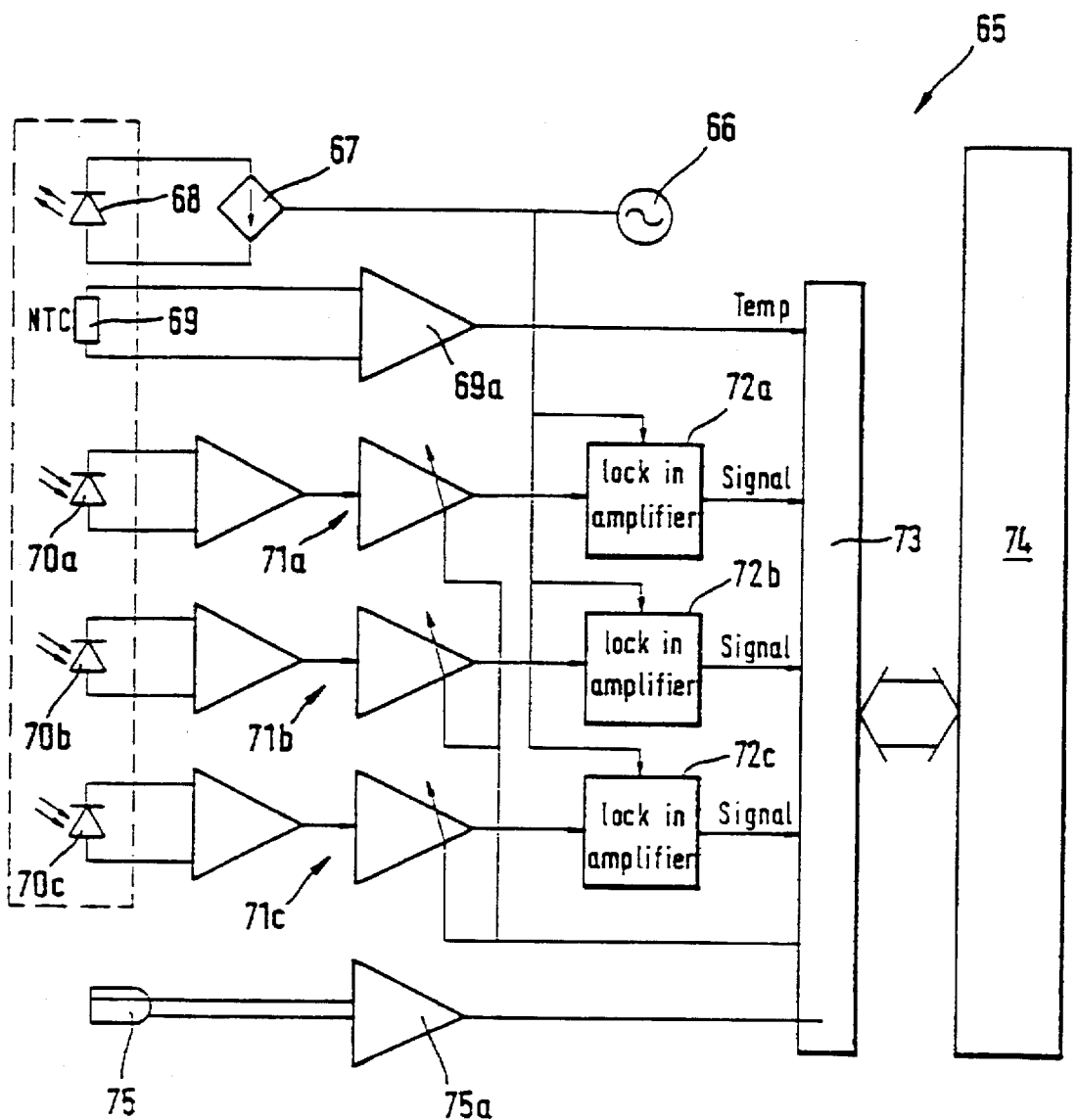

FIG. 20 A block circuit diagram of a suitable electronic circuitry for the invention.

FIG. 21 A view corresponding to FIG. 14 of an alternative embodiment of a measuring head.

FIG. 22 A cross-section through the light-transmission area 34 of the measuring head shown in FIG. 21 along the line S.

FIG. 23 A detail representation of an alternative embodiment in a crossection corresponding to FIG. 22.

FIGS. 1 to 3 have been explained before.

An optically heterogeneous biological matrix 10 is represented symbolically as a rectangular block in FIGS. 4 to 7. It is bounded by an upper boundary surface 11a and a lower boundary surface 11b. In reality, the biological matrix can for example be blood. In this case the boundary surfaces run along the inner walls of an optically transparent vessel (cuvette) in which the blood is contained for in vitro analytical investigation. If the biological matrix is a tissue, the surface of the tissue forms the boundary surface.

FIGS. 4 to 8 clarify different variants of possible arrangements of one or more irradiation sites 12 and one or more detection sites 14 on a biological matrix 10 in a spatially resolved measurement of multiply scattered light according to the invention. Here the irradiation sites 12 usually exist as narrow, longitudinal irradiation fields 12a–12f and the detection sites as longitudinal, narrow detection fields 14a–14i. A longitudinal shape of this kind for the transition sites 12, 14 has proved to be a good and practicable compromise between the demands of adequate spatial resolution and those of an adequate intensity of the irradiated or measured light at an acceptable cost of production. The length of a transition field should be at least three times, preferably at least ten times, as great as its width. The average width of the transition fields is preferably not more than 2 mm, particularly preferably not more than 1 mm. Similar considerations, however, also apply in the case where the transition sites have a point shape or a circular shape as far as no special features of the longitudinal shape have to be considered.

In the embodiment represented in FIG. 4 the primary light 15 is irradiated into the matrix 10 through an irradiation field 12a and the secondary light 17 is detected emerging from two detection fields 14a and 14b running at different measurement distances D1 and D2 from the irradiation field 12a.

In the embodiment represented in FIG. 5 the primary light 15 also enters through an irradiation field 12b into the biological matrix 10 and the secondary light 17 emerges therefrom through two detection fields 14c and 14d, where the detection fields are arranged at different lateral measurement distances D1 and D2 from the irradiation field 12b. However, the detection fields 14c and 14d in this embodiment are located on the boundary surface 11b lying opposite the boundary surface 11a through which the primary light 15 is irradiated. In such an embodiment the irradiation field and detection field are preferably arranged so that in at least two pairs of transition fields, the surface of the output field is not crossed by any straight lines crossing the surface of the irradiation field perpendicularly. In other words, the detection field should not be situated exactly opposite the input irradiation field, but should always be displaced laterally to this.

The arrangement of FIG. 4 can be described as a measurement 'in reflection' and that of FIG. 5 as a measurement 'in transmission', where these terms are to be understood in the sense discussed before.

If the biological matrix is a tissue, particularly cutaneous (skin) tissue, in general only one boundary surface bounding the matrix (namely the surface of the skin) is accessible in an in vivo analytical determination. This is particularly the case for those parts of the body preferred in the invention, namely the fingertips, trunk, nailbeds, sclerae or the inside of the upper arm of humans. In these cases only measurement by the reflection method—which is in any case preferred in the present invention—is possible, where the primary light is irradiated and the secondary light is detected on the same boundary surface of the matrix. In exceptional cases, for example on the ear-lobes, lips, tongue or folds of skin (e.g. between thumb and forefinger), two opposite boundary surfaces 11a and 11b are also available in the in vivo analytical determination on cutaneous tissue.

In the embodiment represented in FIG. 6 the primary light is irradiated into the biological matrix 10 through two irradiation fields 12c and 12d and the secondary light 17 emerging from the detection field 14e is detected. The irradiation fields 12d and 12c are arranged at different measurement distances D1 and D2 from the detection field 14e, so that, in this embodiment again the possibility is provided to measure the secondary light emerging from the detection field 14e in dependence on the measurement distance from the corresponding irradiation field 12c or 12d, in order to derive from the two measured intensities a quantity which is a measure of the concentration of the analyte in the biological matrix.

In this embodiment obviously the portions of secondary light resulting from the primary light of the two different irradiation fields must be separated from each other. This can be achieved by irradiation at separate times, in which case the irradiations must however be carried out within a sufficiently narrow time range in the sense of the definition given above. Alternatively, it is also possible to use differently modulated light (for example with two different frequencies) for the irradiation into the two irradiation fields 12c and 12d and to measure the resulting secondary light portions by a corresponding modulation-dependent (frequency-dependent) detection, for example by means of a lock-in amplifier.

In all embodiments shown in FIGS. 4 to 6, the maximum measurement distance D2 between an irradiation site and a detection site in a spatially resolved measurement of scattered light is 30 mm. The shorter distance D1 should be at least 0.5 mm, preferably at least 1 mm. In other words, in an embodiment according to FIG. 1 with a fixed irradiation site 12 and differing detection sites 14 the detection sites should lie in a detection area 16 (indicated by a dashed line in the Figure) that includes that part of the boundary surface 11a that has a distance of at least 0.5 mm, preferably at least 1 mm and of at most 30 mm from the centre of the irradiation site 12. In an embodiment according to FIG. 6 with a fixed detection site 14 and varying irradiation sites 12 the corresponding values apply for the irradiation area 18 indicated by a dashed line.

FIG. 7 shows an embodiment in which a large number of differing detection fields 14f, at different distances from an irradiation field 12e, can be arranged on the boundary surface 11a within a detection area 22. In the illustrated case, this is achieved by imaging the detection area 22 in an image plane 24 using an optical imaging system symbolised as a lens 23. In the image plane 24 there is a two-dimensional arrangement 26 of light-sensitive elements which are preferably charge-coupled devices (CCD's) 25.

Due to the optical imaging a specific detection field corresponds to a specific area of the CCD matrix 25. For example, the field 14f is imaged on row 25f and the field 14g on row 25g of the CCD matrix 25. A specific detection field can thus easily be selected by processing the measured intensity signals of those photosensitive elements at which the desired detection field is imaged in order to derive the concentration.

It becomes clear from this embodiment that the terms 'irradiation field' and 'detection field' or 'irradiation site' and 'detection site' are to be interpreted geometrically. It is not absolutely necessary that components of the analytical apparatus touch the boundary surface of the biological matrix, for example the surface of the skin, and come into contact with the irradiation site or the detection site. What is necessary is simply that the irradiation site and the detection site are defined for each measurement distance, that is, that the primary light is irradiated at a defined and limited irradiation site and the secondary light is detected at a defined site in such a way that the defined limited area of the boundary surface (the detection site) is known from which the secondary light is emerging, the intensity of which is being measured. Such a measurement must be carried out in at least two different light paths between the irradiation site and the detection site in order to derive quantities characteristic of the analytical determination from the measured intensities.

FIG. 8 clearly shows that the narrow longitudinal shape of the fields need not necessarily be straight (as in FIGS. 4–7). An input irradiation field 12f in the form of a section of a circular ring is shown in a view vertically onto a boundary surface. Two detection fields 14h and 14i likewise run in the form of sections of circular rings at different distances from the input irradiation field 12f. The circular rings here are concentric and the detection fields 14h and 14i therefore run equidistantly from the input irradiation field 12f.

A good spatial resolution is obtained when the light is irradiated at an input irradiation site that is as narrow and limited as possible (point-shaped) and the detection site forms a circle or section of a circle around this input irradiation site. Conversely, it is in principle also possible to work with a circular input irradiation site and a point-shaped detection site located in the centre of this circle, in which case, however, the signal intensity is lower.

When—as shown in FIGS. 4 to 7—input irradiation fields and detection fields run straight and parallel to one another, the spatial resolution is lower because obviously not only portions of light arriving from the directly opposite section of the input irradiation field but also from longitudinally displaced sections of the input irradiation field are measured at each point of a longitudinal detection site. In practical tests of the invention, it was however found that good results can nevertheless be attained with such an arrangement. The embodiment shown in FIG. 8 represents a compromise solution to the problem, as the spatial resolution here is better by virtue of the curved concentric shape than with the straight form of the fields as shown in FIGS. 4 to 7.

Other curved shapes are also possible, though these should generally fulfil the condition that the transition fields (measured from centre to centre) run at constant distances D1 and D2. As long as the input irradiation site and the detection site are located on the same boundary surface of the biological matrix, the input irradiation site and the detection site should always be separated by a band 47 (FIG. 8) of essentially constant width. The width of the detection field measured across the shortest connection to the input irradiation field (hence in the direction of the distance arrows D1 and D2) should be less than 2 mm and preferably less than 1 mm.

FIGS. 9 to 12 show, in a schematic representation (in plan view on the boundary surface), different arrangements in which redundant measurements, that is, several spatially resolved scattered light measurements with equal measurement distances and equal measurement wavelengths but different irradiation- and/or detection sites, are possible.

Figure 9:
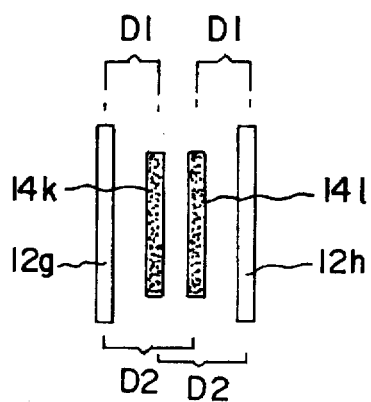

In the embodiment according to FIG. 9, two longitudinal rectangular detection fields 14k and 14l are arranged at equal distances between two likewise rectangular irradiation fields 12g and 12h. All transition fields run parallel to each other. A first measurement distance D1 can be set up both by combination of the irradiation field 12g and the detection field 14k and by combination of the irradiation field 12h and the detection field 14l. A second, larger measurement distance D2 is produced by combination of the transition fields 12g with 14l and 12h with 14k.

Figure 10:
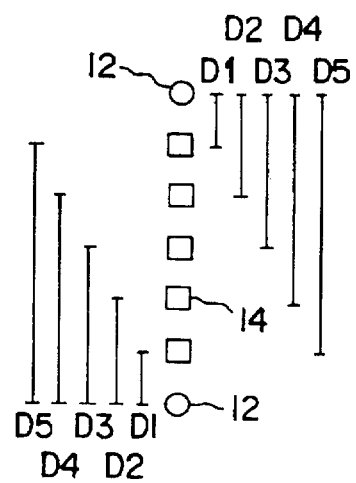

FIG. 10 shows a corresponding linear arrangement with two outer irradiation sites 12. Five detection sites 14 are arranged at equal distances on the connecting line between the irradiation sites 12. In this case all the transition sites are dots with a generally round cross-section. The symbolic representation as squares and circles merely facilitates differentiation of the irradiation sites 12 and the detection sites 14. Five different measuring distances D1 to D5 can be set up in two different ways in this embodiment with different irradiation and detection sites, as shown in the Figure.

Figure 11:
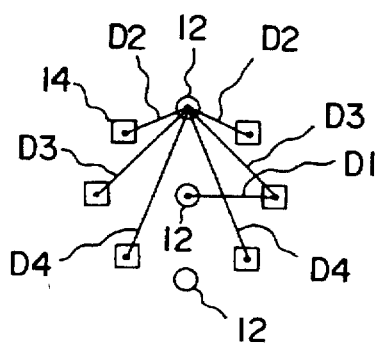

In the embodiment represented of FIG. 11 three irradiation sites 12 are combined with six detection sites. The irradiation sites 12 are arranged at equal distances on a straight line. In the case shown the detection sites are located on a circle around the central irradiation site. They should generally be distributed symmetrically like mirror images on either side of the straight line on which the irradiation sites are arranged. A six-fold redundancy is produced in this arrangement in relation to the central irradiation site 12, as each of the detection sites 14 is positioned at an equal distance D1 from the central irradiation site. A four-fold redundancy for three different measurement distances D2, D3 and D4 is produced in total with regard to the upper and lower irradiation sites 12 (for the sake of clarity only the measurement distances to the upper irradiation site are shown in the Figure), as each of these irradiation sites can be combined with two detection sites positioned at the corresponding distances D2 to D4. Such an arrangement allows a high redundancy with relatively few components, as each measurement distance can be set up with more than two different combinations of irradiation site 12 and detection site 14.

Particularly preferred are arrangements with at least three different irradiation sites and at least three different detection sites, which allow the setting up of a plurality of different measurement distances each with at least three different pairings of irradiation site and detection site. An at least three-fold redundancy has the advantage that it generally allows detection of any deviation of one of the scattered light measurements from the other two scattered light measurements. Generally speaking, the irradiation sites and the detection sites can in principle be interchanged. However, for reasons of cost, it is more advantageous to provide more detection sites than irradiation sites.

Figure 12:
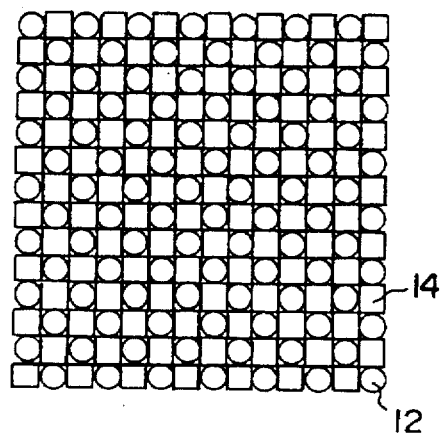

In the embodiment represented in FIG. 12 a large number of irradiation sites 12 and detection sites 14 are arranged alternately in a chequered pattern in such a way that each irradiation site is surrounded by four detection sites and each detection site is surrounded by four irradiation sites. Such an arrangement allows to provide numerous different measurement distances, each with many different combinations of irradiation sites and detection sites.

Redundant measurement arrangements, such as those represented in FIGS. 9 to 12, allow the recognition and elimination of potential measurement errors arising from inhomogeneities in the biological matrix. To this end several measurements are made with equal measurement distances but different irradiation and/or detection sites and compared. If the structure of the investigated biological matrix is homogeneous, an equal intensity of the detected secondary light (with equal intensity of the irradiated primary light) should be measured. Deviations permit the conclusion that interfering structures (for example, scars, hairs or fibromae), which falsify the measurement result, are present in the investigated area of the surface of the skin. This can be corrected in various ways. For example, the measuring head placed on the skin can be placed in another position in order to change the investigated area of the surface of the skin ("measurement focus") so that the inhomogeneities lie outside the measurement focus. With adequate redundancy (always more than two-fold) it is also possible to recognize and eliminate isolated individual measurement results as outliers without variation of the measurement focus. Finally, with a very large number of measurements a mean value determination is possible. These measures can obviously also be combined.

When—as in the embodiment shown in FIG. 7 and FIG. 10—many different distances between the irradiation site and the detection site can be used, the course of the measured intensity I can easily be plotted in relation to the measurement distance D between the detection site and the irradiation site. A practically continuous curve I(D) representing the profile of the detected secondary light in relation to the distance between the particular irradiation site and the corresponding detection site results when a large number of closely adjacent detection sites can be set. In this case a suitable regression algorithm previously known for such purposes (for example, PLS) can be used for deriving the quantity which is characteristic of the analytical determination.

The embodiment with a detection area in which a large number of different sub-areas can be used as detection fields can obviously be designed without the optical imaging system 23 shown in FIG. 7. In particular, it is possible to position a two-dimensional arrangement of light-sensitive elements and/or light emitters immediately above the boundary surface 11a provided that, with the aid of suitable means such as shields, light guides or the like, care is taken to ensure that each light-sensitive element detects the secondary light emerging from a specified limited sub-area of the boundary surface 11a. A design of this kind is particularly suitable for the embodiments in accordance with FIGS. 10 to 12 and can be integrated in a module.

It is advantageous for the invention if the dependence of the intensity I of the secondary light from the distance D between the irradiation site and the detection site is determined with good spatial resolution. Both the irradiation site 12 and the detection site 14 should therefore have a small width of not more than 2 mm, preferably of not more than 1 mm, across the straight line connecting the two fields. The various detection fields and/or irradiation fields by which the various measurement distances are formed should preferably be separated spatially (not overlapping).

An embodiment in which a large number of different detection sites can be detected by a two-dimensional arrangement of photosensitive elements (as in FIG. 7 and FIG. 12) opens up a series of additional possibilities, which will be described hereafter. In these, the detection sites should be closely adjacent to each other. At least two, preferably at least four, particularly preferably at least eight different detection sites per cm should be provided in at least one dimension, preferably in two dimensions.

Firstly, it is possible to find again a defined measurement position on the surface of the skin ("measurement focus"). For example, characteristic structures of the surface can be recognized with the aid of a pattern recognition method. Alternatively, or additionally, a mark can be made on the skin (for example, by means of a tatoo invisible in normal light but contrasting in NIR light) which is recognized and the position of which is detected by the two-dimensional arrangement of photosensitive elements.

Secondly, various intensity profiles, which for example extend in a radial direction from a central irradiation site, can be compared in order to recognize and eliminate negative influences of heterogeneities present in the skin. Out of a large number of radial intensity distributions detected and determined by means of the two-dimensional arrangement of photosensitive elements, preferably only those with a continuous intensity profile are used.

Furthermore, because of the large amount of data produced by such a two-dimensional arrangement of photosensitive elements, modern mathematical evaluation methods can be used which allow the differentiation of various influential factors by means of the intensity distribution. These include the possibility of distinguishing between the influences of the tissue structure and those of the glucose concentration.

An important possibility is the separation of the change in intensity caused by absorption on the one hand and by scattering on the other hand. For this purpose intensity profiles have to be measured at different wavelengths by means of a two-dimensional arrangement of photosensitive elements. It may be advantageous to employ an arrangement in which a large number of irradiation sites and detection sites are located close together in the form of a matrix, with light of at least two different wavelengths being irradiated and detected alternately in the matrix. Apart from the use of several wavelengths, this arrangement basically corresponds to FIG. 12, except that it is not essential to use a regular chessboard pattern with a regularly alternating arrangement of irradiation sites and detection sites.

The number of different wavelengths preferably corresponds to the number of major disturbing (interfering) components plus one additional wavelength. At least four different wavelengths are preferred in such an embodiment, having regard to the three most important interfering components Hb, HbO2 and H2O. From such measurement results the influences of the scattering coefficient and of the absorption coefficient can be separated from each other by means of known methods. In consideration of the knowledge of the present invention about the MSAGD effect it is possible with such a two-dimensional multi-wavelength measurement to achieve substantial elimination of the disturbing influences of the strongly absorbing substances in the determination of the glucose concentration and, conversely, likewise to achieve substantial elimination of the interference caused by changes of the glucose concentration, for example in a determination of the Hb- and $HbO_2$ concentration which is based on the spectral analysis.

FIGS. 13 to 15 show a practical embodiment of a measuring head 30 which is suitable for the invention and especially suitable for the in vivo determination of glucose in human tissue.

The measuring head 30 has a generally circular disc-shaped skin contact element 31 fixed to a measuring head housing 32. During use the skin contact element 31 is placed on the surface of the skin 33 and lightly pressed against it. In its centre there is a square light-transmission area 34, which is shown enlarged in FIG. 15. It contains five rows 35 to 39 of optical fibers 29, which in the illustrated example each consist of 32 fibers with an average diameter of 0.25 mm. The optical fibers 29 are usually arranged in the light-transmission area 34 so that their end surfaces lie flush in a common level contact surface 42 and are in direct contact with the skin when the skin contact element 31 is placed on the skin 33.

The row 35 of optical fibers defines one irradiation site. The optical fibers 29 of this row are for this purpose connected by a cable 40 to a central unit (not shown) in which there is a preferably monochromatic light source, for example a light emitting diode or a laser diode, the light of which is irradiated into the optical fibers 29 which, together with the light source (which is not shown), form a light irradiation means 27 for controlled illumination of a defined irradiation site on the surface of the skin.

Some of the optical fibers of row 35 are preferably used to control the constancy of the light source. In a practical embodiment 16 of the 32 fibers were used for irradiating the light and the remaining 16 fibers were used for controlling the intensity of the light, the latter being bundled separately from the former and guided to a photosensitive element.

As measuring receivers or detectors photodiodes arranged in the measuring head 30 can for example be used. Preferably a common measuring receiver is provided for each row 36 to 39 of optical fibers 29 defining a possible detection site. The optical fibers of these rows are bundled together and guided to a measuring receiver by which the light emerging from these optical fibers is detected. Rows 36 to 39 of the optical fibers 29, together with the measuring receiver (not shown), form a detecting means 28 for specific measurement of the secondary light emerging at a defined detection site.

The end surfaces of the optical fibers of rows 35 to 39 terminate flush with the skin contact surface 42 bounding the light-emission area 34 from below or stand slightly proud of this. This prevents light from passing along the surface of the skin directly from the irradiation site defined by row 35 to one of the detection sites defined by rows 36 to 39. Obviously the glass fibers of different rows within the measuring head 30 are also carefully optically separated from one another so that no primary light can be transmitted to the detecting means.

The measuring head 30 is particularly useful for continuous monitoring of the blood glucose of diabetics. For this purpose it is fixed to a suitable site, for example to the skin on the upper abdomen. This can for example be done with adhesive tape. The contact surface 42 should be pressed on with sufficiently firm, even pressure.

Surrounding light is blocked by means of a ring 31a on the skin contact element 31 with a diameter substantially greater than that of the light-transmission area 34. It consists of an opaque material and ends with its edge 31b on the skin. Alternatively or additionally the primary light can be modulated with a specified frequency and selectively detected by a narrow band and frequency-dependent detection circuitry (for example a lock-in amplifier) to minimize influences of interfering light.

The light-emission area 34 is enclosed by a ring-shaped heating surface 41, in which there is a surface resistance heater. This can be regulated to a predetermined temperature, for example 37° C., with the aid of an NTC resistor and a PD regulator.

FIG. 16 shows results of analytical determinations obtained on the one hand by a reference method and on the other hand by an apparatus according to the invention (embodiment according to FIGS. 13 to 15). The concentration C in millimoles/liter is plotted against time t in minutes. The continuous line 45 marks the results of an enzymatic analytical determination of the glucose in the test subject's blood used as the reference method, whilst the rectangular markings 46 are measurement points made with the device according to the invention.

The following measurement conditions were used in an example according to the invention.

A measuring head as shown in FIGS. 13 to 15 was used. Light of a wavelength of 805 nm from a 1 mW light-emitting diode was irradiated through row 35 of the optical fibers into the skin and detected by rows 38 and 39. The distances of rows 38 and 39 from row 35 (and consequently the distances of the detection fields from the irradiation field) were 3 mm and 5 mm respectively.

The ratio of the intensity I1 of the light measured on row 39 to the intensity I2 of the light measured on row 38 was formed in order to derive a quantity R characteristic of the concentration. This quantity R=I1/I2 was subjected to linear calibration according to the formula C=a*R+b.

The result represented in FIG. 16 shows an excellent agreement of the quantities measured conventionally in vitro in the blood with those measured according to the invention in vivo in the tissue over a period of five and a half hours.

FIGS. 17 and 18 show a measurement support 50 for determination of the glucose concentration in a finger 51. Here the finger 51 is inserted into a perfectly fitting channel 52 formed in a supporting block 53 made of aluminium or some other good heat-conducting material, which is brought to a specified temperature preferably somewhat above normal body temperature (above 37° C.) with a thermostatically controlled heating system (which is not shown).

The side elements 54 laterally confining the channel 52 can be moved so that the width of the channel 52 can be adjusted to fit the patient's finger 51. Fixing elements 55 are provided for fixing the finger 51 from above. These are biased towards the finger 51 by the tension of a spring (not shown).

The supporting block 53, the side elements 54 and the fixing elements 55 all together form, together with a stop 56 limiting the channel 52 in the direction of insertion, a clamp by which the finger 51 is positioned in the most accurately reproducible position possible relative to the measuring device generally designated as 58.

An irradiation means 27 is formed in the measuring device 58 by a light-emitting diode (not shown) and by a light guide-channel 59, through which primary light is directed on to a flat, circular input irradiation site of about 1 mm diameter on the underside of the tip of the finger 51. Three detection sites 14 concentrically surrounding the input irradiation site 12 as semicircular detection fields 14k–14m are provided in a detection area 16. The detecting means 28, shown more clearly in FIG. 19, again each consist here of a row of tightly packed optical fibers 29, the terminal surfaces of which surround the light guide-channel 59 in the skin contact surface 42 semicircularly, and of a photoelectric detector for the light from each of the detection sites 14k, 14l and 14m. The irradiation means 27 are carefully screened from the detecting means 28 by a partition 62.

An infrared temperature sensor 60 is directed towards a temperature-measuring site 61, which should be as close to the detection area 16 as possible.

In experimental work with the invention it was found to be important that the contact pressure between the particular part of the body and the skin contact surface of the measuring device is sufficiently high and reproducible. In the embodiment represented in FIGS. 17 and 18 this is achieved by means of a pressure weight 63 pressing on the fingertip from above. A pressure of about 300 p (Pond) has proved suitable.

FIG. 20 shows by way of example the block circuit diagram of an electronic circuit 65 suitable as an evaluation means for a measuring device according to the invention. A current-voltage transformer 67 that is controlled by an oscillator 66 supplies the current for the light-emitting diode 68 serving as the light source. The temperature of the light-emitting diode 68 can optionally be monitored by a NTC 69 in order to improve the constancy of the intensity of the emitted light.

The output signals of the measurement receivers (photodiodes) 70a–70c are connected via preamplifiers 71a–71c to lock-in amplifiers 72a–72c, to which the signal of the oscillator 66 is also connected as a reference. The output signals of the lock-in amplifiers 72a–72c are digitalised by an A/D transformer unit 73 and fed to a central microcomputer unit 74. The latter also receives the signals of the NTC 69 (amplified by a preamplifier 69a) and of a temperature sensor 75 (amplified by a preamplifier 75a) for measurement of the temperature in the detection area. The temperature sensor 75 (like the IR sensor 60 of the embodiment illustrated in FIG. 17) preferably operates without direct contact.

In the alternative embodiment illustrated in FIGS. 21 and 22, semiconductor light receivers 80 (for example photodiodes) are positioned as detecting means 28 alternately with semiconductor light emitters 81 (for example light-emitting diodes) as light irradiation means 27 in a matrix-type pattern directly on the skin contact surface 42 in the light-transmission region 34 of the skin-contact element 31 of a measuring head. As can clearly be seen in FIG. 22, the semiconductor light emitters 80 and the semiconductor light receivers 81 are integrated in the same component 83, the arrangement being shown merely schematically without any constructional details. The component can be manufactured in practice by an integration method customary in electronics, for example by monolithic integration in a chip or using hybrid technology. What is important is that both the light emitters 81 and the light receivers 80 are in direct optical contact with the surface of the skin and are screened against the adjoining elements, so that they can irradiate light into a defined irradiation site and detect it at a defined detection site respectively.

The illustrated embodiment allows to make measurements at two different wavelengths, for example in order to better eliminate interference due to strongly absorbing substances as explained in more detail above. In the figures the semiconductor light emitters 81a and semiconductor light receivers 80a for the first wavelength are shown in white, while the semiconductor light emitters 81b and semiconductor light receivers 80b for the second wavelength are shown shaded.

According to a further preferred embodiment (especially in devices having a plurality of irradiation sites) light of two or more different wavelengths (such as from different LEDs) can be irradiated at the same irradiation site. This can be accomplished by using optical means such as light guide fibers to combine the light of different light sources at one location. FIG. 23 shows as an example two light-emitting diodes 85, 86 directed to the two arms of a commercially available Y-shaped light combining element 87 from which the primary light is irradiated through skin contact element 31 into a skin (not shown) against which surface 42 of element 31 is pressed. Alternatively the common irradiation of a plurality of wavelengths at one irradiation site can be accomplished for example by aiming a plurality of light sources onto one hole (defining an irradiation site) in a skin contact element.

In all embodiments shown in the Figures, both the setting of different measurement distances D and the selection of different wavelengths (if necessary) is accomplished without moving parts. This is usually advantageous from the point of view of cost and reliability. Alternatives with moving parts are of course also possible in the context of the invention. Different measurement distances D can thus be set by moving either the light irradiation means 27 or the detection means 28, for example with the aid of a spindle drive. The functional dependence I(D) of the intensity I from the measurement distance D can in this case be determined by stepwise adjustment of the drive.

In particular cases, for example for the detection of disturbing quantities, it may also be appropriate to provide means for the irradiation and/or detection of a narrow-band wavelength range. A grating-type monochromator can be provided for this purpose on the primary side or on the secondary side.

We claim:

1. An apparatus for determination of a glucose concentration in a biological matrix, said apparatus comprising:
    irradiation means for irradiating light as primary light into a biological matrix through a boundary surface thereof;
    detection means for measuring an intensity of light emerging as secondary light through the boundary surface of the biological matrix, said detection means being configured to detect light from said irradiation means after the light has propagated along a light path within the biological matrix;
    data processing means coupled to said irradiation means and said detection means for processing measurement signals from said detection means;
    said irradiation means being configured to provide spatially limited illumination of an irradiation site of said boundary surface, said detection means being configured for spatially limited measurement of the secondary light emerging at a detection site of said boundary surface, wherein the detection site is located relative to the irradiation site such that the secondary light is multiply scattered at scattering centers in the biological matrix;
    wherein said irradiation means and said detection means are configured to provide at least two different light paths within the biological matrix during detection measurements between respective irradiation and detection sites, and configured to perform at least two detection measurements wherein the light paths of said at least two detection measurements are different, and are further configured to generate separate measurement signals by said detection means for each of said at least two detection measurements;
    wherein said data processing means converts the separate measurement signals measured by said detection means with said different light paths into a signal corresponding to a glucose concentration in the biological matrix.

2. An apparatus according to claim 1, comprising at least two of said irradiation means, each of said at least two irradiation means having essentially corresponding wavelengths, said at least two irradiation means being configured to irradiate light onto different irradiation sites.

3. An apparatus according to claim 1, comprising at least two of said detection means, said at least two detection means being configured to measure secondary light emerging from the biological matrix at two different detection sites.

4. An apparatus according to claim 1, further comprising light blocking means disposed between the irradiation means and the detection means to prevent transmission of primary light from the irradiation means to the detection means by any path other than through the biological matrix.

5. An apparatus according to claim 1, wherein a dimension of the irradiation site in a spatial direction which is defined by the shortest distance to the detection site is no more than 2 mm.

6. An apparatus according to claim 1, wherein a dimension of the irradiation site in a spatial direction which is defined by the shortest distance to the detection site is no more than 1 mm.

7. An apparatus according to claim 1, wherein a dimension of the detection site in a spatial direction which is defined by the shortest distance to the irradiation site is no more than 2 mm.

8. An apparatus according to claim 1, wherein a dimension of the detection site in a spatial direction which is defined by the shortest distance to the irradiation site is no more than 1 mm.

9. An apparatus according to claim 1, wherein a distance between a center of an irradiation site and a center of a detection site forming one of said at least two light paths is no greater than 30 mm.

10. An apparatus according to claim 1, wherein a distance between a center of an irradiation site and a center of a detection site forming one of said at least two light paths is no greater than 15 mm.

11. An apparatus according to claim 1, wherein a distance between a center of an irradiation site and a center of a detection site forming one of said at least two light paths is no greater than 10 mm.

12. An apparatus according to claim 1, wherein the detection site has a long, narrow configuration such that a length thereof is significantly greater than a width thereof.

13. An apparatus according to claim 12, wherein said detection site at least partially surrounds the irradiation site in an arcuate equidistant configuration.

14. An apparatus according to claim 1, wherein at least one of a set of at least three irradiation means and a set of at least three detection means are provided, and configured wherein at least three different light paths are formed between respective pairings of corresponding irradiation means and detection means.

15. An apparatus according to claim 1, wherein at least two irradiation means are provided for irradiating primary light at different irradiation sites and at least two detection means are provided for detecting secondary light emerging at different detection sites, said irradiation means and said detection means being configured wherein at least two pairings of corresponding irradiation means and corresponding detection means are provided for each of at least two different distances between the corresponding irradiation sites and the corresponding detection sites.

16. An apparatus according to claim 1, wherein said detection means comprises a light receiver located in a light transmission area of a skin contact element.

17. An apparatus according to claim 16, comprising a plurality of said detection means, said plurality of detection means being attached to the skin contact element forming a two-dimensional arrangement of photosensitive elements.

18. An apparatus according to claim 1, wherein said irradiation means comprises a semiconductor light emitter located in a light-transmission area of a skin contact element.

19. An apparatus according to claim 1, wherein said data processing means converts the measurement signals into the signal corresponding to the glucose concentration based upon a dependence of an intensity of the measurement signals in the at least two detection measurements upon a relative position of the irradiation site and detection site in the at least two detection measurements.

20. An apparatus according to claim 19, wherein said data processing means separates absorption and scattering of said primary light as factors which influence the intensity of the measurement signals in the at least two detection measurements, said data processing means separating the absorption and scattering based upon an intensity profile of the secondary light as a function of a measurement distance of the detection site from the irradiation site.

21. An apparatus according to claim 1, wherein the primary light irradiated by the irradiation means has a wavelength between 400 nm and 2500 nm.

22. An apparatus according to claim 21, wherein the wavelength of the primary light is between 400 nm and 600 nm.

23. An apparatus according to claim 21, wherein the wavelength of the primary light is between 750 nm and 920 nm.

24. An apparatus according to claim 23, wherein the wavelength of the primary light is between 780 nm and 825 nm.

25. An apparatus according to claim 23, wherein the wavelength of the primary light is between 850 and 900 nm.

26. An apparatus according to claim 21, wherein the wavelength of the primary light is between 1050 nm and 1350 nm.

27. An apparatus according to claim 21, wherein the wavelength of the primary light is between 1200 nm and 1300 nm.

28. An apparatus according to claim 21, wherein the wavelength of the primary light is between 1600 nm and 1800 nm.

29. An apparatus according to claim 28, wherein the wavelength of the primary light is between 1630 nm and 1770 nm.

30. An apparatus according to claim 29, wherein the wavelength of the primary light is between 1630 nm and 1670 nm.

31. An apparatus according to claim 29, wherein the wavelength of the primary light is between 1730 nm and 1770 nm.

32. An apparatus according to claim 1, wherein the primary light irradiated by the irradiation means has a wavelength in a spectral region wherein glucose concentration has a minimal effect on the optical absorption coefficient of the biological matrix.

* * * * *